US008067015B2

(12) United States Patent
Balaban

(10) Patent No.: US 8,067,015 B2
(45) **Date of Patent: *Nov. 29, 2011**

(54) **METHODS AND COMPOSITIONS FOR THE TREATMENT AND PREVENTION OF *STAPHYLOCOCCUS* AND OTHER BACTERIAL INFECTIONS**

(76) Inventor: Naomi Balaban, Davis, CA (US)

(*) Notice: Subject to any disclaimer, the term of this patent is extended or adjusted under 35 U.S.C. 154(b) by 996 days.

This patent is subject to a terminal disclaimer.

(21) Appl. No.: 11/441,229

(22) Filed: May 26, 2006

(65) Prior Publication Data

US 2007/0009569 A1 Jan. 11, 2007

Related U.S. Application Data

(63) Continuation of application No. 10/358,448, filed on Feb. 3, 2003, now Pat. No. 7,323,179, which is a continuation-in-part of application No. 09/839,695, filed on Apr. 19, 2001, now Pat. No. 7,067,135, which is a continuation-in-part of application No. 09/054,331, filed on Apr. 2, 1998, now Pat. No. 6,291,431.

(60) Provisional application No. 60/068,094, filed on Dec. 19, 1997.

(51) Int. Cl.

| | |
|---|---|
| ***A61K 39/00*** | (2006.01) |
| ***A61K 39/38*** | (2006.01) |
| ***A61K 39/09*** | (2006.01) |
| ***A61K 39/02*** | (2006.01) |
| ***A61K 39/085*** | (2006.01) |

(52) U.S. Cl. ............... 424/243.1; 424/184.1; 424/236.1; 424/237.1

(58) Field of Classification Search ........................ None
See application file for complete search history.

(56) References Cited

U.S. PATENT DOCUMENTS

| | | | | |
|---|---|---|---|---|
| 3,845,770 | A | 11/1974 | Theeuwes et al. | |
| 3,995,651 | A | 12/1976 | Adams | |
| 4,034,756 | A | 7/1977 | Higuchi et al. | |
| 4,111,202 | A | 9/1978 | Theeuwes | |
| 4,235,871 | A | 11/1980 | Papahadjopoulos et al. | |
| 4,320,759 | A | 3/1982 | Theeuwes | |
| 4,449,983 | A | 5/1984 | Cortese et al. | |
| 4,501,728 | A | 2/1985 | Geho et al. | |
| 4,837,028 | A | 6/1989 | Allen | |
| 5,019,369 | A | 5/1991 | Presant et al. | |
| 5,023,088 | A | 6/1991 | Wong et al. | |
| 5,049,322 | A * | 9/1991 | Devissaguet et al. | 264/4.1 |
| 5,364,838 | A | 11/1994 | Rubsamen | |
| 6,291,431 | B1 | 9/2001 | Balaban et al. | |
| 6,447,786 | B1 | 9/2002 | Novick et al. | |
| 6,475,434 | B1 * | 11/2002 | Darouiche | 422/28 |
| 6,689,878 | B2 | 2/2004 | Balaban et al. | |
| 6,706,289 | B2 * | 3/2004 | Lewis et al. | 424/501 |
| 6,747,129 | B1 | 6/2004 | Balaban et al. | |
| 7,067,135 | B2 | 6/2006 | Balaban | |
| 7,270,969 | B2 | 9/2007 | Watt et al. | |
| 7,323,179 | B2 * | 1/2008 | Balaban | 424/234.1 |
| 7,534,857 | B2 * | 5/2009 | Balaban | 530/300 |
| 7,824,691 | B2 * | 11/2010 | Balaban | 424/234.1 |
| 2002/0090376 | A1 | 7/2002 | Kaniga et al. | |
| 2002/0102271 | A1 | 8/2002 | Balaban et al. | |
| 2004/0072748 | A1 | 4/2004 | Balaban | |
| 2004/0077534 | A1 | 4/2004 | Balaban | |
| 2006/0165716 | A1 | 7/2006 | Telford et al. | |
| 2006/0252691 | A1 * | 11/2006 | Balaban | 514/12 |
| 2007/0009566 | A1 * | 1/2007 | Balaban | 424/423 |
| 2007/0009567 | A1 * | 1/2007 | Balaban | 424/423 |
| 2007/0009569 | A1 * | 1/2007 | Balaban | 424/423 |
| 2007/0015685 | A1 * | 1/2007 | Balaban | 514/2 |
| 2007/0071768 | A1 * | 3/2007 | Balaban | 424/190.1 |
| 2007/0092572 | A1 * | 4/2007 | Balaban et al. | 424/487 |
| 2007/0092575 | A1 * | 4/2007 | Balaban et al. | 424/489 |
| 2007/0231335 | A1 | 10/2007 | Beutler et al. | |
| 2007/0293435 | A1 * | 12/2007 | Balaban et al. | 514/18 |
| 2008/0138332 | A1 * | 6/2008 | Balaban | 424/133.1 |
| 2008/0152701 | A1 * | 6/2008 | Balaban | 424/450 |
| 2008/0219976 | A1 * | 9/2008 | Balaban | 424/133.1 |

FOREIGN PATENT DOCUMENTS

| | | |
|---|---|---|
| EP | 0 395 099 B1 | 10/1990 |
| EP | 1 188 831 A2 | 3/2002 |
| WO | 96/10579 | 4/1996 |
| WO | 97/44349 | 11/1997 |
| WO | 99/32133 | 7/1999 |
| WO | 2005/009396 A2 | 2/2005 |

OTHER PUBLICATIONS

Lowy, J. CLin. Invest., May 2003, 111/9:1265-1273.*

Kiran et al, International J. Artificial Organs, Sep. 2008, 31/9:761-770 abstract only.*

Balaban et al, Antimicrobial Agents and Chemotherapy.*

Kiran et al, Molecular Pharmacology, 2008, 73:1578-1586.*

Cirioni et al, Antimicrobial Agents and Chemotherapy, Dec. 2007, 51/12:4518-4520.*

Simonetti et al, Antimicrobial Agents and Chemotherapy, Jun. 2008, 52/6:2205-2211.*

Balaban et al, Int. J. Artif. Organs, 2008, 31:761-770.*

International Search Report dated Dec. 10, 2008, received in International Application No. PCT/US07/82801.

Balaban et al., "Autocrine regulation of toxin synthesis by *Staphylococcus aureus." Proc. Nat'l Acad. Sci. USA* 92: 1619-1623 (1995).

Balaban et al., "Translation of RNAIII, the *Staphylococcus aureus agr* regulatory RNA molecule, can be activated by a 3'-end deletion." *FEMS Microbiol. Lett.* 133: 155-161 (1995).

Balaban et al., "Autoinducer of virulence as a target for vaccine and therapy against *Staphylococcus aureus." Science* 280: 438-440 (1998).

U.S. Appl. No. 11/414,350, filed May 1, 2006, Balaban.

U.S. Appl. No. 11/440,093, filed May 25, 2006, Balaban.

U.S. Appl. No. 11/441,229, filed May 26, 2006, Balaban.

Balaban et al., "Prevention of diseases caused by *Staphylococcus aureus* using the peptide RIP." *Peptides* 21: 1301-1311 (2000).

Balaban et al., "Activation and inhibition of the *Staphylococcus agr* system." *Science* 287: 391a (2000).

(Continued)

*Primary Examiner* — N. M Minnifield

(74) *Attorney, Agent, or Firm* — DLA Piper LLP (US)

(57) ABSTRACT

The invention features methods and compositions for treatment or prevention of infection by, or disease caused by infection with, certain species of bacteria, including in particular bacteria in which a RAP-type and/or TRAP-type molecule plays a role in pathogenesis. This includes *Staphylococcus* species.

3 Claims, 18 Drawing Sheets

OTHER PUBLICATIONS

Balaban et al., "Regulation of *Staphylococcus aureus* pathogenesis via target of RNAIII-activating Protein (TRAP)." *J. Biol. Chem*. 276: 2658-2667 (2001).
Balaban et al., "Prevention of *Staphylococcus aureus* biofilm on dialysis catheters and adherence to human cells." *Kidney Int'l* 63: 340-345 (2003).
Balaban et al., "Use of the quorum-sensing inhibitor RNAIII-inhibiting peptide to prevent biofilm formation in vivo by drug-resistant *Staphylococcus epidermidis." J. Infect. Dis*. 187: 625-630 (2003).
Balaban et al., "A chimeric peptide composed of a dermaseptin derivative and an RNA III-inhibiting peptide prevents graft-associated infections by antibiotic-resistant staphylococci." *Antimicrob. Agents Chemother*. 48: 2544-2550 (2004).
Cirioni et al., "Prophylactic efficacy of topical temporin A and RNAIII-inhibiting peptide in a subcutaneous rat pouch model of graft infection attributable to staphylococci with intermediate resistance to glycopeptides." *Circulation* 108: 767-771 (2003).
Costerton et al., "Bacterial biofilms: a common cause of persistent infections." *Science* 284: 1318-1322 (1999).
Dell'Acqua et al., "Suppression of drug-resistant staphylococcal infections by the quorum-sensing inhibitor RNAIII-inhibiting peptide." *J. Infect. Dis*. 190: 318-320 (2004).
Domenico et al., "BisEDT and RIP act in synergy to prevent graft infections by resistant staphylococci." *Peptides* 25: 2047-2053 (2004).
Ghiselli et al., "RNAIII-inhibiting peptide and/or nisin inhibit experimental vascular graft infection with methicillin-susceptible and methicillin-resistant *Staphylococcus epidermidis." Eur. J. Vasc. Endovasc. Surg*. 27: 603-607 (2004).
Giacometti et al., "RNA III inhibiting peptide inhibits in vivo biofilm formation by drug-resistant *Staphylococcus aureus." Antimicrob. Agents Chemother*. 47: 1979-1983 (2003).
Giacometti et al., "RNAIII-inhibiting peptide improves efficacy of clinically used antibiotics in a murine model of staphylococcal sepsis." *Peptides* 26: 169-175 (2005).
Gov et al., "RNAIII inhibiting peptide (RIP), a global inhibitor of *Staphylococcus aureus* pathogenesis: structure and function analysis." *Peptides* 22: 1609-1620 (2001).
Gov et al., "Quorum sensing in Staphylococci is regulated via phosphorylation of three conserved histidine residues." *J. Biol. Chem*. 279: 14665-14672 (2004).
Hartman et al., "Quorum sensing: potential means of treating gram-negative infections?" *Lancet* 351: 848-849 (1998).
Ji et al., "Cell density control of *Staphylococcus* virulence mediated by an octapeptide pheromone." *Proc. Nat'l Acad. Sci. USA* 92: 12055-12059 (1995).
Ji et al., "Bacterial interference caused by autoinducing peptide variants." *Science* 276: 2027-2030 (1997).
Korem et al., "Characterization of RAP, a quorum sensing activator of *Staphylococcus aureus." FEMS Microbiol. Lett*. 223: 167-175 (2003).
Korem et al., "Transcriptional profiling of target of RNAIII-activating protein, a master regulator of staphylococcal virulence." *Infect. Immun*. 73: 6220-6228 (2005).
Lee, "An experimental vaccine that targets staphylococcal virulence." *Trends Micrbiol*. 6: 461-463 (1998).
Mayville et al., "Structure-activity analysis of synthetic autoinducing thiolactone peptides from *Staphylococcus aureus* responsible for virulence." *Proc. Nat'l Acad. Sci. USA* 96: 1218-1223 (1999).
Morfeldt et al., "Activation of alpha-toxin translation in *Staphylococcus aureus* by the *trans*-encoded antisense RNA, RNAIII." *EMBO J*. 14(18): 4569-4577 (1995).
Novick et al., "Synthesis of staphylococcal virulence factors is controlled by a regulatory RNA molecule." *EMBO J*. 12(120): 3967-3975 (1993).
Novick et al., "Virulence gene regulation by peptides in staphylococci and other Gram-positive bacteria." *Curr. Opin. Microbiol*. 2: 40-45 (1999).
Otto, "Quorum-sensing control in Staphylococci—a target for antimicrobial drug therapy?" *FEMS Microbiol. Lett*. 241: 135-141 (2004).
Panlilio et al., "Methicillin-resistant *Staphylococcus aureus* in U.S. hospitals, 1975-1991." *Infect. Control Hosp. Epidemiol*. 13: 582-586 (1992).
Ribeiro et al., "Treatment efficacy of the lead RNAIII-inhibiting peptide YSPWTNF-$NH_2$ in acquired *Staphylococcus aureus* sepsis: a histopathological assessment." *Peptides* 24: 1829-1836 (2003).
Silverstein et al., "Host defense against bacterial and fungal infections." Microbiology, B.D. Davis, et al., eds., 4th ed., J.B. Lippincott Co., Philadelphia, PA, Chapter 21, pp. 485-505 (1980).
Smith et al., "Induction and inhibition of *Pseudomonas aeruginosa* quorum sensing by synthetic autoinducer analogs." *Chem Biol*. 10: 81-89 (2003).
Strauss, "A possible new approach to combating Staph infections." *Science* 280: 379 (1998).
Vieira-Da-Motta et al., "RNAIII inhibiting peptide (RIP) inhibits *agr*-regulated toxin production." *Peptides* 22: 1621-1627 (2001).
Vieira-Da-Motta et al., "Repression of enterotoxin production in *Staphylococcus aureus* by quorum sensing effectors." 41st Interscience Conference on Antimicrobial Agents and Chemotherapy, Abstract B-955, p. 46 (Sep. 22-25, 2001).
Yang et al., "Inhibition of *Staphylococcus aureus* pathogenesis in vitro and in vivo by RAP-binding peptides." *Peptides* 24: 1823-1828 (2003).
Yang et al., "A novel peptide screened by phage display can mimic TRAP antigen epitope against *Staphylococcus aureus* infections." *J. Biol. Chem*. 280: 27431-27435 (2005).
Yang et al., "A novel peptide isolated from phage library to substitute a complex system for a vaccine against staphylococci infection." *Vaccine* 24: 1117-1123 (2006).
Balaban et al., "Prevention of *Staphylococcal* Biofilm-Associated Infections by the Quorom Sensing Inhibitor RIP," *Clin. Orth.*, 437:48-54, 2005.
Bixler et al., "B Cell Recognition of Protein Antigens—Perspectives from the Submolecular Level," *Synthetic Vaccines*, 1:39-71, 1987.
Blyhe et al., "Benchmarking B Cell Epitope Prediction: Underperformance of Existing Methods," *Protein Science*, 14:246-248, 2005.
Bowie et al., "Deciphering the Message in Protein Sequences: Tolerance to Amino Acid Substitutions," *Science*, 247:1306-1310, 1990.
Burgess et al., "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue," *Journal of Cell Biology*, 111 :2129-2138, 1990.
Chakraborty et al., "Coordinate Regulation of Virulence Genes in *Listeria Monocyogenes* Requires the Product of the prfA Gene," *J. Bacteriology*, 174(2):568-574, 1992.
Creighton, T. E., In: *Proteins: Structures and Molecular Properties*, 314-315, 1984.
Creighton, T. E., In: *Protein Structure: A Practical Approach*, 184-186, 1989.
Fraser et al., "Identification and Characterization of an ATP Binding Cassette L-Carnitine Transporter in *Listeria Monocytogenes*, " *Appl. Environ. Microbiol.*, 66(11):4696-4704, 2000.
Greenspan et al., "Defining Epitopes: It's Not As Easy As It Seems," *Nature Biotechnology*, 17:936-937, 1999.
Houghten et al., "Relative Importance of Position and Individual Amino Acid Residues in Peptide Antigen-Antibody Interactions: Implications in the Mechanism of Antigenic Drift and Antigenic Shift," *Vaccine* 86, 21-25, 1986.
Kumar et al, Amino Acid Variations at a Single Residue in an Autoimmune Peptide Profoundly Affect its Properties: T-Cell Activation, Major Histocompatibility Complex Binding, and Ability to Block Experimental Allergic Encephalomyelitis, *PNAS*, 87:1337-1341, 1990.
Lazar et al., "Transforming Growth Factor $\alpha$: Mutation of Aspartic Acid 47 and Leucine 48 Results in Different Biological Activities," *Molecular and Cellular Biology*, 8:1247-1252, 1988.

Nosoh, Y et al, In: *Protein Stability and Stabilization through Protein Engineering*, 197, 1991.
Scott et al., "CBS Domains Form Energy-Sensing Modules whose Binding of Adenosine Ligands is Disrupted by Disease Mutations," *J. Clin. Invest.*, 113:274-284, 2004.
Solomon et al., "Isolation and Characterization of Mutants of the *Bacillus Subtilis* Oligopeptide Permease with Altered Specifity of Oligopeptide Transport," *J. Bacteriology*, 185(21):6425-6433, 2003.

* cited by examiner

```
RAP_RN6390B   MAIKKYKPITNGRRNMTSLDFAEITKTTPEKSLLKPLPKKAGRNNQGKLTVRHHGGGHKR  60
RplB_StaEpi   MALKKYKPITNGRRNMTTLDFAEITKTTPEKSLLQPLPKRAGRNNQGKLTVRHHGGGHKR  60
RplB_LisMon   MAIKKYKPTTNGRRHMTSSDFAEITTSTPEKSLLRPLKKKAGRNNQGKLTVRHHGGGHKR  60
RplB_BacSub   MAIKKYKPSSNGRRGMTTSDFAEITTDKPEKSLLAPLHKKGGRNNQGKLTVRHQGGGHKR  60
RplB_EntFae   MAIKKYKPTTNGRRNMTSSDFAEITTSTPEKSLLQPLKNNAGRNNNGRITVRHQGGGHKR  60
RplB_StrPyo   MGIKVYKPTTNGRRNMTSLDFAEITTSTPEKSLLVSLKSKAGRNNNGRITVRHQGGGHKR  60
RplB_LacLac   MGIKVYKPTTNGRRNMTGSDFAEITTSTPEKSLLVSMSKTAGRNNTGRITVRHHGGGHKR  60
RplB_CloAce   MAVRGFKPTSPARRQMTVSTFEEITTDVPEKSLLVSLNNKAGRNNNGKITVRHRGGGNRN  60
RplB_E_coli   MAVVKCKPTSPGRRHVVKVVNPELHKGKPFAPLLEKNSKSGGRNNNGRITTRHIGGGHKQ  60
              *.:   ** : .** :.     *: .  *  .**     . .**** *::*.** ***::.

RAP_RN6390B   QYRVIDFKRNKDGINAKVDSIQYDPNRSANIALVVYADGEKRYIIAPKGLEVGQIVESGA 120
RplB_StaEpi   QYRVIDFKRNKDGIIAKVDSIQYDPNRSANIALLVYADGEKRYIIAPKGLQVGQTVESGA 120
RplB_LisMon   QYRVIDFKRNKDGIPGRVATIEYDPNRSANIALINYADGEKRYIIAAKGLEVGQTIYSGA 120
RplB_BacSub   QYRVIDFKRDKDGIPGRVATVEYDPNRSANIALINYADGEKRYILAPKGIQVGTEVMSGP 120
RplB_EntFae   QYRVIDFKRNKDNVAAVVKTIEYDPNRSANIALVHYEDGVKAYILAPKGLEVGMRLVSGP 120
RplB_StrPyo   HYRLIDFKRNKDGVEAVVKTIEYDPNRTANIALVHYTDGVKAYIIAPKGLEVGQRIVSGP 120
RplB_LacLac   KYRVIDFKRTTDNVVAKVATIEYDPNRTANIALIVYSNGVKSYILAPKGLEVGMTVVSGP 120
RplB_CloAce   KYRLIDFKRNKDGVPAKVTTIEYDPNRSAYIALVVYADGEKRYIIAPTKLSVGDTVVSGP 120
RplB_E_coli   AYRIVDFKRNKDGIPAVVERLEYDPNRSANIALVLYKDGERRYILAPKGLKAGDQIQSGV 120
               **::**** .*.: . *  ::*****:* ***: * :* : **:*.. :..*  : **

RAP_RN6390B   EADIKVGNALPLQNIPVGTVVHNIELKPGKGGQIARSAGASAQVLGKEGKYVLIRLRSGE 180
RplB_StaEpi   EADIKVGNALPLQNIPVGTVIHNIELKPGKGGQLARSAGASSQVLGKEGKYVLIRLRSGE 180
RplB_LisMon   EADIKVGNALELKDIPVGTVIHNIEMKPGKGGQLVRSAGTSAQVLGKEGKYVLIRLNSGE 180
RplB_BacSub   EADIKVGNALPLINIPVGTVVHNIELKPGKGGQLVRSAGTSAQVLGKEGKYVLVRLNSGE 180
RplB_EntFae   EADIKVGNALPLENIPVGTVIHNIEMKPGKGGQLIRSAGTSAQVLGKEGKYVLIRLNSGE 180
RplB_StrPyo   DADIKVGNALPLANIPVGTVVHNIELKPGKGGELVRAAGASAQVLGQEGKYVLVRLQSGE 180
RplB_LacLac   EADIKVGNALPLANIPVGTLIHNIELKPGKGGQLVRSAGASAQVLGSEGKYTLVRLQSGE 180
RplB_CloAce   DADIKIGNALPIKNIPVGTVIHNVELAAGKGAQLVRAAGSSAQLMAKEGNYAQLRLPSGE 180
RplB_E_coli   DAAIKPGNTLPMRNIPVGSTVHNVEMKPGKGGQLARSAGTYVQIVARDGAYVTLRLRSGE 180
              :* ** **:* : :****: :**:*: .***.:: *:**:  *::. :* *. :** ***

RAP_RN6390B   VRMILSTCRATIGQVGNLQHELVNVGKAGRSRWKGIRPTVRGSVMNPNDHPHGGGEGRAP 240
RplB_StaEpi   VRMILSTCRATIGQVGNLQHELVNVGKAGRSRWKGVRPTVRGSVMNPNDHPHGGGEGRAP 240
RplB_LisMon   VRMILATCRATIGQVGNEQHELINIGKAGRSRWMGKRPTVRGSVMNPNDHPHGGGEGKAP 240
RplB_BacSub   VRMILSACRASIGQVGNEQHELINIGKAGRSRWKGIRPTVRGSVMNPNDHPHGGGEGRAP 240
RplB_EntFae   VRMILATCRATIGSVGNEQHELINIGKAGRSRWMRKRPTVRGSVMNPNDHPHGGGEGKTP 240
RplB_StrPyo   VRMILGTCRATIGTVGNEQQSLVNIGKAGRSRWKGIRPTVRGSVMNPNDHPHGGGEGKAP 240
RplB_LacLac   VRMILSTCRATIGVVGNEQQSLINLGKAGRTRHMGIRPTVRGSVMNPNDHPHGGGEGRQP 240
RplB_CloAce   MRYVRIECRATIGTVSNLTHDIVNIGKAGRKRHMGIRPTVRGSVMNPNDHPHGGGEGKSP 240
RplB_E_coli   MRKVEADCRATLGEVGNAEHMLRVLGKAGAARWRGVRPTVRGTAMNPVDHPHGGGEGRN- 239
              :* :    ***::* *.*   : :   :****   *     ******:.*** *********:

RAP_RN6390B   IGRPSPMSPWGKPTLGKKTRRGKKSSDKLIVRGRKKK 277   Ident=100% Simil=100%
RplB_StaEpi   IGRPSPMSPWGKPTLGKKTRRGKKSSDKLIVRGRKKK 277   Ident= 96% Simil= 99%
RplB_LisMon   IGRKSPMSPWGKPTLGYKTRKKNNNSDKFIVRRRKKK 277   Ident= 84% Simil= 91%
RplB_BacSub   IGRKSPMSPWGKPTLGFKTRKKKNKSDKFIVRRRKNK 277   Ident= 82% Simil= 88%
RplB_EntFae   IGRKAPVSPWGQPAIGYKTRNKKAKSDKLIVRRRT-K 276   Ident= 78% Simil= 87%
RplB_StrPyo   VGRKAPSTPWGKPALGLKTRNKKAKSDKLIVRRRNEK 277   Ident= 77% Simil= 86%
RplB_LacLac   VGRKSPMTPWGKPALGLKTRNKKAKSSKLIVR-RIND 276   Ident= 76% Simil= 85%
RplB_CloAce   VGRPGPVTPWGKPALGYKTRKNKKYSDKLIVKRRNDK 277   Ident= 66% Simil= 80%
RplB_E_coli   FGKH-PVTPWGVQTKGKKTRSNK-RTDKFIVRRRS-K 273   Ident= 58% Simil= 76%
              .*:  * :***  : * ***  :  :.*:**: *. :
```

Figure 1

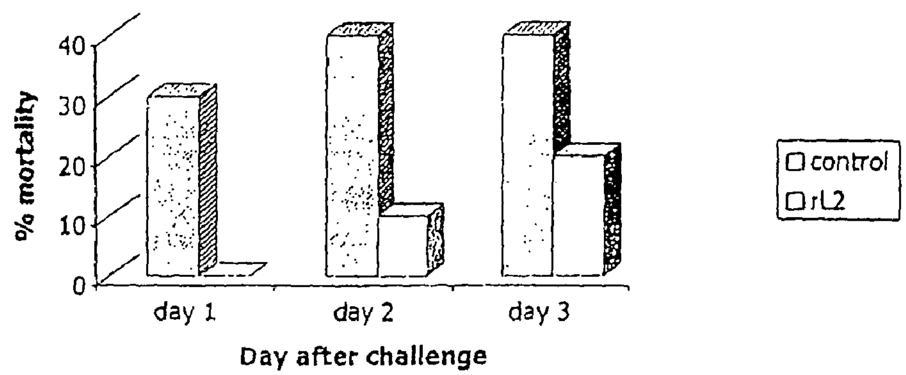
Fig. 4: Vaccination of Balb/c mice with rL2 and challenge with 2x10e9 S. aureus SD
40
30
20
10
0
% mortality
day 1
day 2
day 3
Day after challenge
control
rL2
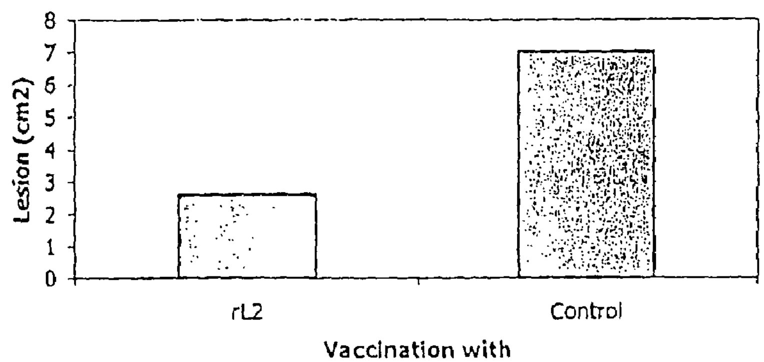
Fig. 5: Development of lesion in rL2 vaccinated animals that survived a challenge of 2x10e9 S. aureus cells
8
7
6
5
4
3
2
1
0
Lesion (cm2)
rL2
Control
Vaccination with

Figure 9

```
           *************:*******:*:*****::*:*******: :***************
8325-4     MKKLYTSYGTYGFLHQIKINNPTHQLFQFSASDTSVIFEETDGETVLKSPSIYEVIKEIG  60 }
COL        MKKLYTSYGTYGFLHQIKINNPTHQLFQFSASDTSVIFEETDGETVLKSPSIYEVIKEIG  60 } I
Mu50       MKKLYTSYGTYGFLHQIKINNPTHQLFQFSASDTSVIFEETDGETVLKSPSIYEVIKEIG  60 }
SA-#7      MKKLYTSYGTYGFLHQIKINNPTHQLFQFSASDTSVIFEETDGETVLKSPSIYEVIKEIG  60 }
MRSA252    MKKLYTSYGTYGFLNQIKINNPSHHLFQFSTADSSVIFEETEENTVLKSPSIYEVIKEIG  60 }
SA-#15     MKKLYTSYGTYGFLNQIKINNPSHHLFQFSTADSSVIFEETEENTVLKSPSIYEVIKEIG  60 } II
SA-#12     MKKLYTSYGTYGFLNQIKINNPSHHLFQFSTADSSVIFEETEEKTVLKSPSIYEVIKEIG  60 }
SE_RP62A   MY-LYTSYGTYQFLNQIKLNHQERSLFQFSTNDSSIILEESEGKSILKHPSSYQVIDSTG  59
           *  ******** **:***:*:  : *****: *:*:*:**:: :::** *: *:**.. *

            *.*.*************.*************:************.***********
8325-4     EFSEHHFYCAIFIPSTEDHAYQLEKKLISVDDNFRNFGGFKSYRLLRPAKGTTYKIYFGF 120 }
COL        EFSEHHFYCAIFIPSTEDHAYQLEKKLISVDDNFRNFGGFKSYRLLRPAKGTTYKIYFGF 120 } I
Mu50       EFSEHHFYCAIFIPSTEDHAYQLEKKLISVDDNFRNFGGFKSYRLLRPAKGTTYKIYFGF 120 }
SA-#7      EFSEHHFYCAIFIPSTEDHAYQLEKKLISVDDNFRNFGGFKSYRLLRPAKGTTYKIYFGF 120 }
MRSA252    AFNEDHFYCAIFIPSTEDHVYQLEKKLISVDDNFKNFGGFKSYRLLRPVKGTTYKIYFGF 120 }
SA-#15     AFNEDHFYCAIFIPSTEDHVYQLEKKLISVDDNFKNFGGFKSYRLLRPVKGTTYKIYFGF 120 } II
SA-#12     AFNEDHFYCAIFIPSTEDHVYQLEKKLISVDDNFKNFGGFKSYRLLRPVKGTTYKIYFGF 120 }
SE_RP62A   EFNEHHFYSAIFVPTSEDHRQQLEKKLLHVDVPLSNFGGFKSYRLLKPTEGSTYKIYFGF 119
            *.*.***.***:*::***  ******: **  : **********:*.:*:********

           ***::*****:****:*****:************************
8325-4     ADRHAYEDFKQSDAFNDHFSKDALSHYFGSSGQHSSYFERYLYPIKE--------- 167 aa }
COL        ADRHAYEDFKQSDAFNDHFSKDALSHYFGSSGQHSSYFERYLYPIKE--------- 167 aa } I
Mu50       ADRHAYEDFKQSDAFNDHFSKDALSHYFGSSGQHSSYFERYLYPIKE--------- 167 aa }
SA-#7      ADRHAYEDFKQSDAFNDHFSKDALSHYFGSSGQHSSYFERYLYPIKE--------- 167 aa }
MRSA252    ADRQTYEDFKNSDAFKDHFSKEALSHYFGSSGQHSSYFERYLYPIKE--------- 167 aa }
SA-#15     ADRQTYEDFKNSDAFKDHFSKEALSHYFGSSGQHSSYFERYLYPIKE--------- 167 aa } II
SA-#12     ADRQTYEDFKNSDAFKDHFSKEALSHYFGSSGQHSSYFERYLYPIKEGSSSFMVGR 176 aa }
SE_RP62A   ANRTAYEDFKASDIFNENFSKDALSQYFGASGQHSSYFERYLYPIEDH-------- 167 aa
           *:* :***** ** *:::***:***:***:**************::
```

S. aureus (NCTC8325, COL, N315, Mu50, MRSA252, MSS476, clinical isolates ## 7, 11 and 15)
hemE
traP
~ 0.9 kB
ecsB
S. aureus #12 (a clinical isolate; this study)
hemE
traP
IS1181
~ 2.4 kB
ecsB
S. epidermidis
hemE
traP
cadD
~ 2.0 kB
ecsB
Listeria monocytogenes and L. innocua
hemE
LMO2213
LIN2316
~0.74 kB
ecsB
Bacillus subtilis
hemE
pbpF
yhgC
yhgB
~ 6.7 kB
yhfA
yhaA
ecsC
ecsB
Bacillus anthracis
hemE
pbpF
yhgC
~10 ORFs
~ 14.7 kB
ecsC
ecsB In vivo phosphorylation of Listeria spp.

1. L. monocytogenes strain 1001
2. L. monocytogenes strain Scott A
3. L. ivanovii strain 3009

Table 1. Prevention of *S. epidermidis* infection using RIP-coated Dacron grafts in the presence or absence of local (A) or parenteral (B) antibiotic prophylaxis.

A. Local prophylaxis

Bacterial concentration is x $10^4$ CFU/ml ± SD

| Strain⇨<br>Treatment⇩ | GISE<br>x$10^4$ CFU/ml± SD | MRSE<br>x$10^4$ CFU/ml±SD | MSSE<br>x$10^4$ CFU/ml±SD |
|---|---|---|---|
| Control (untreated) | 680 ± 190 | 810 ± 220 | 730 ± 64 |
| RIP | 6.2 ± 2.4 | 0.74 ± 0.18 | 0.91 ± 0.23 |
| Levofloxacin | 280 ± 40 | 6.8 ± 2.5 | 4.2 ± 2.1 |
| Levofloxacin + RIP | 4.9 ± 0.79 | 0.26 ± 0.057 | 0.58 ± 0.072 |
| Mupirocin | 0.07 ± 0.018 | 0.035 ± 0.014 | 0.064 ± 0.015 |
| Mupirocin + RIP | 0.000 ± 0 | 0.000 ± 0 | 0.000 ± 0 |
| Rifampicin (Refampin) | 84 ± 27 | 0.8 ± 0.37 | 0.73 ± 0.2 |
| Rifampicin + RIP | 5.9 ± 2.2 | 0.064 ± 0.013 | 0.031 ± 0.01 |
| Quinupristin-Dalfopristin (Q/D) | 0.0069 ± 0.0013 | 0.0048 ± 0.001 | 0.0026 ± 0.0003 |
| Quinupristin-Dalfopristin + RIP | 0.000 ± 0 | 0.000 ± 0 | 0.000 ± 0 |

Table 1B. Parenteral prophylaxis

Bacterial concentration is x $10^4$ CFU/ml ± SD

| Strain⇨<br>Treatment⇩ | GISE<br>x$10^4$CFU/ml± SD | MRSE<br>x$10^4$ CFU/ml±SD | MSSE<br>x$10^4$ CFU/ml± SD |
|---|---|---|---|
| Control (untreated) | 680 ± 190 | 810 ± 220 | 730 ± 64 |
| RIP | 6.2 ± 2 | 0.74 ± 0.18 | 0.91 ± 0.23 |
| Cefazolin | 590 ± 200 | 370 ± 120 | 0.64 ± 0.19 |
| Cefazolin + RIP | 4.2 ± 1.6 | 0.35 ± 0.11 | 0.058 ± 0.034 |
| Teicoplanin | 57 ± 24 | 0.072 ± 0.008 | 0.0084 ± 0.0004 |
| Teicoplanin + RIP | 2.4 ± 1.8 | 0.000 ± 0 | 0.000 ± 0 |
| Imipenem | 89 ± 36 | 4 ± 1.8 | 0.73 ± 0.2 |
| Imipenem + RIP | 4 ± 2.5 | 0.088 ± 0.017 | 0.043 ± 0.012 |
| Levofloxacin | 480 ± 170 | 3.9 ± 1.4 | 3.5 ± 1.1 |
| Levofloxacin + RIP | 3.9 ± 3.3 | 0.29 ± 0.037 | 0.29 ± 0.055 |

Figure 15

TABLE 2. RIP prevents Dacron-graft associate *S. epidermidis* (A) and *S. aureus* (B) infections.

A.

| Strain⇨ Treatment⇩ | GISE $\times 10^4$ CFU/ml±SD | MRSE $\times 10^4$ CFU/ml±SD | MSSE $\times 10^4$ CFU/ml±SD |
|---|---|---|---|
| Control (untreated) | 880 ± 240 | 680 ± 110 | 710 ± 150 |
| RIP local | 0.46 ± 0.13 | 0.087 ± 0.023 | 0.08 ± 0.024 |
| RIP parenteral | 0.31 ± 0.6 | 0.052 ± 0.017 | 0.067± 0.019 |
| RIP local + RIP parenteral | 0.00 ± 0 | 0.00 ± 0 | 0.00 ± 0 |

B.

| Strain⇨ Treatment⇩ | GISA $\times 10^4$ CFU/ml±SD | MRSA $\times 10^4$ CFU/ml±SD | MSSA $\times 10^4$ CFU/ml±SD |
|---|---|---|---|
| Control (untreated) | 4000 ± 1700 | 3000 ± 300 | 4900 ± 2100 |
| RIP local | 0.70 ± 0.28 | 0.62 ± 0.21 | 0.55 ± 0.19 |
| RIP parenteral | 0.49 ± 0.11 | 0.29 ± 0.088 | 0.045± 0.009 |
| RIP local + RIP parenteral | 0.00 ± 0 | 0.00 ± 0 | 0.00 ± 0 |

Figure 16

SEQUENCE LISTING

```
<160> NUMBER OF SEQ ID NOS: 32

<210> SEQ ID NO 1
<211> LENGTH: 277
<212> TYPE: PRT
<213> ORGANISM: Staphylococcus aureus

<400> SEQUENCE: 1

Met Ala Ile Lys Lys Tyr Lys Pro Ile Thr Asn Gly Arg Arg Asn Met
  1               5                  10                  15

Thr Ser Leu Asp Phe Ala Glu Ile Thr Lys Thr Thr Pro Glu Lys Ser
             20                  25                  30

Leu Leu Lys Pro Leu Pro Lys Lys Ala Gly Arg Asn Asn Gln Gly Lys
        35                  40                  45

Leu Thr Val Arg His His Gly Gly Gly His Lys Arg Gln Tyr Arg Val
    50                  55                  60

Ile Asp Phe Lys Arg Asn Lys Asp Gly Ile Asn Ala Lys Val Asp Ser
 65                  70                  75                  80

Ile Gln Tyr Asp Pro Asn Arg Ser Ala Asn Ile Ala Leu Val Val Tyr
                 85                  90                  95

Ala Asp Gly Glu Lys Arg Tyr Ile Ile Ala Pro Lys Gly Leu Glu Val
            100                 105                 110

Gly Gln Ile Val Glu Ser Gly Ala Glu Ala Asp Ile Lys Val Gly Asn
        115                 120                 125

Ala Leu Pro Leu Gln Asn Ile Pro Val Gly Thr Val Val His Asn Ile
    130                 135                 140

Glu Leu Lys Pro Gly Lys Gly Gly Gln Ile Ala Arg Ser Ala Gly Ala
145                 150                 155                 160

Ser Ala Gln Val Leu Gly Lys Glu Gly Lys Tyr Val Leu Ile Arg Leu
                165                 170                 175

Arg Ser Gly Glu Val Arg Met Ile Leu Ser Thr Cys Arg Ala Thr Ile
            180                 185                 190

Gly Gln Val Gly Asn Leu Gln His Glu Leu Val Asn Val Gly Lys Ala
        195                 200                 205

Gly Arg Ser Arg Trp Lys Gly Ile Arg Pro Thr Val Arg Gly Ser Val
    210                 215                 220

Met Asn Pro Asn Asp His Pro His Gly Gly Gly Glu Gly Arg Ala Pro
225                 230                 235                 240

Ile Gly Arg Pro Ser Pro Met Ser Pro Trp Gly Lys Pro Thr Leu Gly
                245                 250                 255

Lys Lys Thr Arg Arg Gly Lys Lys Ser Ser Asp Lys Leu Ile Val Arg
            260                 265                 270

Gly Arg Lys Lys Lys
        275


<210> SEQ ID NO 2
<211> LENGTH: 277
<212> TYPE: PRT
```

```
<213> ORGANISM: Staphylococcus epidermidis

<400> SEQUENCE: 2

Met Ala Leu Lys Lys Tyr Lys Pro Ile Thr Asn Gly Arg Arg Asn Met
  1               5                  10                  15

Thr Thr Leu Asp Phe Ala Glu Ile Thr Lys Thr Thr Pro Glu Lys Ser
             20                  25                  30

Leu Leu Gln Pro Leu Pro Lys Arg Ala Gly Arg Asn Asn Gln Gly Lys
         35                  40                  45

Leu Thr Val Arg His His Gly Gly Gly His Lys Arg Gln Tyr Arg Val
     50                  55                  60

Ile Asp Phe Lys Arg Asn Lys Asp Gly Ile Ile Ala Lys Val Asp Ser
 65                  70                  75                  80

Ile Gln Tyr Asp Pro Asn Arg Ser Ala Asn Ile Ala Leu Leu Val Tyr
                 85                  90                  95

Ala Asp Gly Glu Lys Arg Tyr Ile Ile Ala Pro Lys Gly Leu Gln Val
            100                 105                 110

Gly Gln Thr Val Glu Ser Gly Ala Glu Ala Asp Ile Lys Val Gly Asn
        115                 120                 125

Ala Leu Pro Leu Gln Asn Ile Pro Val Gly Thr Val Ile His Asn Ile
    130                 135                 140

Glu Leu Lys Pro Gly Lys Gly Gly Gln Leu Ala Arg Ser Ala Gly Ala
145                 150                 155                 160

Ser Ser Gln Val Leu Gly Lys Glu Gly Lys Tyr Val Leu Ile Arg Leu
                165                 170                 175

Arg Ser Gly Glu Val Arg Met Ile Leu Ser Thr Cys Arg Ala Thr Ile
            180                 185                 190

Gly Gln Val Gly Asn Leu Gln His Glu Leu Val Asn Val Gly Lys Ala
        195                 200                 205

Gly Arg Ser Arg Trp Lys Gly Val Arg Pro Thr Val Arg Gly Ser Val
    210                 215                 220

Met Asn Pro Asn Asp His Pro His Gly Gly Gly Glu Gly Arg Ala Pro
225                 230                 235                 240

Ile Gly Arg Pro Ser Pro Met Ser Pro Trp Gly Lys Pro Thr Leu Gly
                245                 250                 255

Lys Lys Thr Arg Arg Gly Lys Lys Ser Ser Asp Lys Leu Ile Val Arg
            260                 265                 270

Gly Arg Lys Lys Lys
        275


<210> SEQ ID NO 3
<211> LENGTH: 277
<212> TYPE: PRT
<213> ORGANISM: Listeria monocytogenes

<400> SEQUENCE: 3

Met Ala Ile Lys Lys Tyr Lys Pro Thr Thr Asn Gly Arg Arg His Met
  1               5                  10                  15

Thr Ser Ser Asp Phe Ala Glu Ile Thr Thr Ser Thr Pro Glu Lys Ser
             20                  25                  30

Leu Leu Arg Pro Leu Lys Lys Lys Ala Gly Arg Asn Asn Gln Gly Lys
         35                  40                  45

Leu Thr Val Arg His His Gly Gly Gly His Lys Arg Gln Tyr Arg Val
     50                  55                  60

Ile Asp Phe Lys Arg Asn Lys Asp Gly Ile Pro Gly Arg Val Ala Thr
 65                  70                  75                  80
```

```
Ile Glu Tyr Asp Pro Asn Arg Ser Ala Asn Ile Ala Leu Ile Asn Tyr
                85                  90                  95

Ala Asp Gly Glu Lys Arg Tyr Ile Ile Ala Ala Lys Gly Leu Glu Val
            100                 105                 110

Gly Gln Thr Ile Tyr Ser Gly Ala Glu Ala Asp Ile Lys Val Gly Asn
        115                 120                 125

Ala Leu Glu Leu Lys Asp Ile Pro Val Gly Thr Val Ile His Asn Ile
    130                 135                 140

Glu Met Lys Pro Gly Lys Gly Gly Gln Leu Val Arg Ser Ala Gly Thr
145                 150                 155                 160

Ser Ala Gln Val Leu Gly Lys Glu Gly Lys Tyr Val Leu Ile Arg Leu
                165                 170                 175

Asn Ser Gly Glu Val Arg Met Ile Leu Ala Thr Cys Arg Ala Thr Ile
            180                 185                 190

Gly Gln Val Gly Asn Glu Gln His Glu Leu Ile Asn Ile Gly Lys Ala
        195                 200                 205

Gly Arg Ser Arg Trp Met Gly Lys Arg Pro Thr Val Arg Gly Ser Val
    210                 215                 220

Met Asn Pro Asn Asp His Pro His Gly Gly Gly Glu Gly Lys Ala Pro
225                 230                 235                 240

Ile Gly Arg Lys Ser Pro Met Ser Pro Trp Gly Lys Pro Thr Leu Gly
                245                 250                 255

Tyr Lys Thr Arg Lys Lys Asn Asn Asn Ser Asp Lys Phe Ile Val Arg
            260                 265                 270

Arg Arg Lys Lys Lys
        275


<210> SEQ ID NO 4
<211> LENGTH: 277
<212> TYPE: PRT
<213> ORGANISM: Bacillus subtilis

<400> SEQUENCE: 4

Met Ala Ile Lys Lys Tyr Lys Pro Ser Ser Asn Gly Arg Arg Gly Met
  1               5                  10                  15

Thr Thr Ser Asp Phe Ala Glu Ile Thr Thr Asp Lys Pro Glu Lys Ser
            20                  25                  30

Leu Leu Ala Pro Leu His Lys Lys Gly Gly Arg Asn Asn Gln Gly Lys
        35                  40                  45

Leu Thr Val Arg His Gln Gly Gly Gly His Lys Arg Gln Tyr Arg Val
     50                  55                  60

Ile Asp Phe Lys Arg Asp Lys Asp Gly Ile Pro Gly Arg Val Ala Thr
 65                  70                  75                  80

Val Glu Tyr Asp Pro Asn Arg Ser Ala Asn Ile Ala Leu Ile Asn Tyr
                85                  90                  95

Ala Asp Gly Glu Lys Arg Tyr Ile Leu Ala Pro Lys Gly Ile Gln Val
            100                 105                 110

Gly Thr Glu Val Met Ser Gly Pro Glu Ala Asp Ile Lys Val Gly Asn
        115                 120                 125

Ala Leu Pro Leu Ile Asn Ile Pro Val Gly Thr Val Val His Asn Ile
    130                 135                 140

Glu Leu Lys Pro Gly Lys Gly Gly Gln Leu Val Arg Ser Ala Gly Thr
145                 150                 155                 160

Ser Ala Gln Val Leu Gly Lys Glu Gly Lys Tyr Val Leu Val Arg Leu
                165                 170                 175
```

```
Asn Ser Gly Glu Val Arg Met Ile Leu Ser Ala Cys Arg Ala Ser Ile
            180                 185                 190

Gly Gln Val Gly Asn Glu Gln His Glu Leu Ile Asn Ile Gly Lys Ala
        195                 200                 205

Gly Arg Ser Arg Trp Lys Gly Ile Arg Pro Thr Val Arg Gly Ser Val
    210                 215                 220

Met Asn Pro Asn Asp His Pro His Gly Gly Gly Glu Gly Arg Ala Pro
225                 230                 235                 240

Ile Gly Arg Lys Ser Pro Met Ser Pro Trp Gly Lys Pro Thr Leu Gly
                245                 250                 255

Phe Lys Thr Arg Lys Lys Lys Asn Lys Ser Asp Lys Phe Ile Val Arg
            260                 265                 270

Arg Arg Lys Asn Lys
        275


<210> SEQ ID NO 5
<211> LENGTH: 276
<212> TYPE: PRT
<213> ORGANISM: Enterococcus faecalis

<400> SEQUENCE: 5

Met Ala Ile Lys Lys Tyr Lys Pro Thr Thr Asn Gly Arg Arg Asn Met
  1               5                  10                  15

Thr Ser Ser Asp Phe Ala Glu Ile Thr Thr Ser Thr Pro Glu Lys Ser
             20                  25                  30

Leu Leu Gln Pro Leu Lys Asn Asn Ala Gly Arg Asn Asn Asn Gly Arg
         35                  40                  45

Ile Thr Val Arg His Gln Gly Gly Gly His Lys Arg Gln Tyr Arg Val
     50                  55                  60

Ile Asp Phe Lys Arg Asn Lys Asp Asn Val Ala Ala Val Val Lys Thr
 65                  70                  75                  80

Ile Glu Tyr Asp Pro Asn Arg Ser Ala Asn Ile Ala Leu Val His Tyr
                 85                  90                  95

Glu Asp Gly Val Lys Ala Tyr Ile Leu Ala Pro Lys Gly Leu Glu Val
            100                 105                 110

Gly Met Arg Leu Val Ser Gly Pro Glu Ala Asp Ile Lys Val Gly Asn
        115                 120                 125

Ala Leu Pro Leu Glu Asn Ile Pro Val Gly Thr Val Ile His Asn Ile
    130                 135                 140

Glu Met Lys Pro Gly Lys Gly Gly Gln Leu Ile Arg Ser Ala Gly Thr
145                 150                 155                 160

Ser Ala Gln Val Leu Gly Lys Glu Gly Lys Tyr Val Leu Ile Arg Leu
                165                 170                 175

Asn Ser Gly Glu Val Arg Met Ile Leu Ala Thr Cys Arg Ala Thr Ile
            180                 185                 190

Gly Ser Val Gly Asn Glu Gln His Glu Leu Ile Asn Ile Gly Lys Ala
        195                 200                 205

Gly Arg Ser Arg Trp Met Arg Lys Arg Pro Thr Val Arg Gly Ser Val
    210                 215                 220

Met Asn Pro Asn Asp His Pro His Gly Gly Gly Glu Gly Lys Thr Pro
225                 230                 235                 240

Ile Gly Arg Lys Ala Pro Val Ser Pro Trp Gly Gln Pro Ala Ile Gly
                245                 250                 255

Tyr Lys Thr Arg Asn Lys Lys Ala Lys Ser Asp Lys Leu Ile Val Arg
            260                 265                 270
```

```
Arg Arg Thr Lys
        275


<210> SEQ ID NO 6
<211> LENGTH: 277
<212> TYPE: PRT
<213> ORGANISM: Streptococcus pyogenes

<400> SEQUENCE: 6

Met Gly Ile Lys Val Tyr Lys Pro Thr Thr Asn Gly Arg Arg Asn Met
  1               5                  10                  15

Thr Ser Leu Asp Phe Ala Glu Ile Thr Thr Ser Thr Pro Glu Lys Ser
             20                  25                  30

Leu Leu Val Ser Leu Lys Ser Lys Ala Gly Arg Asn Asn Asn Gly Arg
         35                  40                  45

Ile Thr Val Arg His Gln Gly Gly Gly His Lys Arg His Tyr Arg Leu
     50                  55                  60

Ile Asp Phe Lys Arg Asn Lys Asp Gly Val Glu Ala Val Val Lys Thr
 65                  70                  75                  80

Ile Glu Tyr Asp Pro Asn Arg Thr Ala Asn Ile Ala Leu Val His Tyr
                 85                  90                  95

Thr Asp Gly Val Lys Ala Tyr Ile Ile Ala Pro Lys Gly Leu Glu Val
            100                 105                 110

Gly Gln Arg Ile Val Ser Gly Pro Asp Ala Asp Ile Lys Val Gly Asn
        115                 120                 125

Ala Leu Pro Leu Ala Asn Ile Pro Val Gly Thr Val Val His Asn Ile
    130                 135                 140

Glu Leu Lys Pro Gly Lys Gly Gly Glu Leu Val Arg Ala Ala Gly Ala
145                 150                 155                 160

Ser Ala Gln Val Leu Gly Gln Glu Gly Lys Tyr Val Leu Val Arg Leu
                165                 170                 175

Gln Ser Gly Glu Val Arg Met Ile Leu Gly Thr Cys Arg Ala Thr Ile
            180                 185                 190

Gly Thr Val Gly Asn Glu Gln Gln Ser Leu Val Asn Ile Gly Lys Ala
        195                 200                 205

Gly Arg Ser Arg Trp Lys Gly Ile Arg Pro Thr Val Arg Gly Ser Val
    210                 215                 220

Met Asn Pro Asn Asp His Pro His Gly Gly Gly Glu Gly Lys Ala Pro
225                 230                 235                 240

Val Gly Arg Lys Ala Pro Ser Thr Pro Trp Gly Lys Pro Ala Leu Gly
                245                 250                 255

Leu Lys Thr Arg Asn Lys Lys Ala Lys Ser Asp Lys Leu Ile Val Arg
            260                 265                 270

Arg Arg Asn Glu Lys
        275


<210> SEQ ID NO 7
<211> LENGTH: 276
<212> TYPE: PRT
<213> ORGANISM: Lactococcus lactis

<400> SEQUENCE: 7

Met Gly Ile Lys Val Tyr Lys Pro Thr Thr Asn Gly Arg Arg Asn Met
  1               5                  10                  15

Thr Gly Ser Asp Phe Ala Glu Ile Thr Thr Ser Thr Pro Glu Lys Ser
             20                  25                  30
```

```
Leu Leu Val Ser Met Ser Lys Thr Ala Gly Arg Asn Asn Thr Gly Arg
        35                  40                  45

Ile Thr Val Arg His His Gly Gly Gly His Lys Arg Lys Tyr Arg Val
    50                  55                  60

Ile Asp Phe Lys Arg Thr Thr Asp Asn Val Val Ala Lys Val Ala Thr
65                  70                  75                  80

Ile Glu Tyr Asp Pro Asn Arg Thr Ala Asn Ile Ala Leu Ile Val Tyr
                85                  90                  95

Ser Asn Gly Val Lys Ser Tyr Ile Leu Ala Pro Lys Gly Leu Glu Val
            100                 105                 110

Gly Met Thr Val Val Ser Gly Pro Glu Ala Asp Ile Lys Val Gly Asn
        115                 120                 125

Ala Leu Pro Leu Ala Asn Ile Pro Val Gly Thr Leu Ile His Asn Ile
    130                 135                 140

Glu Leu Lys Pro Gly Lys Gly Gly Gln Leu Val Arg Ser Ala Gly Ala
145                 150                 155                 160

Ser Ala Gln Val Leu Gly Ser Glu Gly Lys Tyr Thr Leu Val Arg Leu
                165                 170                 175

Gln Ser Gly Glu Val Arg Met Ile Leu Ser Thr Cys Arg Ala Thr Ile
            180                 185                 190

Gly Val Val Gly Asn Glu Gln Gln Ser Leu Ile Asn Leu Gly Lys Ala
        195                 200                 205

Gly Arg Thr Arg His Met Gly Ile Arg Pro Thr Val Arg Gly Ser Val
    210                 215                 220

Met Asn Pro Asn Asp His Pro His Gly Gly Gly Glu Gly Arg Gln Pro
225                 230                 235                 240

Val Gly Arg Lys Ser Pro Met Thr Pro Trp Gly Lys Pro Ala Leu Gly
                245                 250                 255

Leu Lys Thr Arg Asn Lys Lys Ala Lys Ser Ser Lys Leu Ile Val Arg
            260                 265                 270

Arg Ile Asn Asp
        275


<210> SEQ ID NO 8
<211> LENGTH: 277
<212> TYPE: PRT
<213> ORGANISM: Clostridium acetobutylicum

<400> SEQUENCE: 8

Met Ala Val Arg Gly Phe Lys Pro Thr Ser Pro Ala Arg Arg Gln Met
  1               5                  10                  15

Thr Val Ser Thr Phe Glu Glu Ile Thr Thr Asp Val Pro Glu Lys Ser
            20                  25                  30

Leu Leu Val Ser Leu Asn Asn Lys Ala Gly Arg Asn Asn Asn Gly Lys
        35                  40                  45

Ile Thr Val Arg His Arg Gly Gly Gly Asn Arg Asn Lys Tyr Arg Leu
    50                  55                  60

Ile Asp Phe Lys Arg Asn Lys Asp Gly Val Pro Ala Lys Val Thr Thr
65                  70                  75                  80

Ile Glu Tyr Asp Pro Asn Arg Ser Ala Tyr Ile Ala Leu Val Val Tyr
                85                  90                  95

Ala Asp Gly Glu Lys Arg Tyr Ile Ile Ala Pro Thr Lys Leu Ser Val
            100                 105                 110

Gly Asp Thr Val Val Ser Gly Pro Asp Ala Asp Ile Lys Ile Gly Asn
        115                 120                 125
```

Ala Leu Pro Ile Lys Asn Ile Pro Val Gly Thr Val Ile His Asn Val
130 135 140

Glu Leu Ala Ala Gly Lys Gly Ala Gln Leu Val Arg Ala Ala Gly Ser
145 150 155 160

Ser Ala Gln Leu Met Ala Lys Glu Gly Asn Tyr Ala Gln Leu Arg Leu
165 170 175

Pro Ser Gly Glu Met Arg Tyr Val Arg Ile Glu Cys Arg Ala Thr Ile
180 185 190

Gly Thr Val Ser Asn Leu Thr His Asp Ile Val Asn Ile Gly Lys Ala
195 200 205

Gly Arg Lys Arg His Met Gly Ile Arg Pro Thr Val Arg Gly Ser Val
210 215 220

Met Asn Pro Asn Asp His Pro His Gly Gly Gly Glu Gly Lys Ser Pro
225 230 235 240

Val Gly Arg Pro Gly Pro Val Thr Pro Trp Gly Lys Pro Ala Leu Gly
245 250 255

Tyr Lys Thr Arg Lys Asn Lys Lys Tyr Ser Asp Lys Leu Ile Val Lys
260 265 270

Arg Arg Asn Asp Lys
275

<210> SEQ ID NO 9
<211> LENGTH: 273
<212> TYPE: PRT
<213> ORGANISM: Escherichia coli

<400> SEQUENCE: 9

Met Ala Val Val Lys Cys Lys Pro Thr Ser Pro Gly Arg Arg His Val
1 5 10 15

Val Lys Val Val Asn Pro Glu Leu His Lys Gly Lys Pro Phe Ala Pro
20 25 30

Leu Leu Glu Lys Asn Ser Lys Ser Gly Gly Arg Asn Asn Asn Gly Arg
35 40 45

Ile Thr Thr Arg His Ile Gly Gly Gly His Lys Gln Ala Tyr Arg Ile
50 55 60

Val Asp Phe Lys Arg Asn Lys Asp Gly Ile Pro Ala Val Val Glu Arg
65 70 75 80

Leu Glu Tyr Asp Pro Asn Arg Ser Ala Asn Ile Ala Leu Val Leu Tyr
85 90 95

Lys Asp Gly Glu Arg Arg Tyr Ile Leu Ala Pro Lys Gly Leu Lys Ala
100 105 110

Gly Asp Gln Ile Gln Ser Gly Val Asp Ala Ala Ile Lys Pro Gly Asn
115 120 125

Thr Leu Pro Met Arg Asn Ile Pro Val Gly Ser Thr Val His Asn Val
130 135 140

Glu Met Lys Pro Gly Lys Gly Gly Gln Leu Ala Arg Ser Ala Gly Thr
145 150 155 160

Tyr Val Gln Ile Val Ala Arg Asp Gly Ala Tyr Val Thr Leu Arg Leu
165 170 175

Arg Ser Gly Glu Met Arg Lys Val Glu Ala Asp Cys Arg Ala Thr Leu
180 185 190

Gly Glu Val Gly Asn Ala Glu His Met Leu Arg Val Leu Gly Lys Ala
195 200 205

Gly Ala Ala Arg Trp Arg Gly Val Arg Pro Thr Val Arg Gly Thr Ala
210 215 220

```
Met Asn Pro Val Asp His Pro His Gly Gly Gly Glu Gly Arg Asn Phe
225                 230                 235                 240

Gly Lys His Pro Val Thr Pro Trp Gly Val Gln Thr Lys Gly Lys Lys
                245                 250                 255

Thr Arg Ser Asn Lys Arg Thr Asp Lys Phe Ile Val Arg Arg Arg Ser
            260                 265                 270

Lys


<210> SEQ ID NO 10
<211> LENGTH: 167
<212> TYPE: PRT
<213> ORGANISM: Staphylococcus sp.

<400> SEQUENCE: 10

Met Lys Lys Leu Tyr Thr Ser Tyr Gly Thr Tyr Gly Phe Leu His Gln
  1               5                  10                  15

Ile Lys Ile Asn Asn Pro Thr His Gln Leu Phe Gln Phe Ser Ala Ser
             20                  25                  30

Asp Thr Ser Val Ile Phe Glu Glu Thr Asp Gly Glu Thr Val Leu Lys
         35                  40                  45

Ser Pro Ser Ile Tyr Glu Val Ile Lys Glu Ile Gly Glu Phe Ser Glu
     50                  55                  60

His His Phe Tyr Cys Ala Ile Phe Ile Pro Ser Thr Glu Asp His Ala
 65                  70                  75                  80

Tyr Gln Leu Glu Lys Lys Leu Ile Ser Val Asp Asp Asn Phe Arg Asn
                 85                  90                  95

Phe Gly Gly Phe Lys Ser Tyr Arg Leu Leu Arg Pro Ala Lys Gly Thr
            100                 105                 110

Thr Tyr Lys Ile Tyr Phe Gly Phe Ala Asp Arg His Ala Tyr Glu Asp
        115                 120                 125

Phe Lys Gln Ser Asp Ala Phe Asn Asp His Phe Ser Lys Asp Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu
                165


<210> SEQ ID NO 11
<211> LENGTH: 167
<212> TYPE: PRT
<213> ORGANISM: Staphylococcus sp.

<400> SEQUENCE: 11

Met Lys Lys Leu Tyr Thr Ser Tyr Gly Thr Tyr Gly Phe Leu His Gln
  1               5                  10                  15

Ile Lys Ile Asn Asn Pro Thr His Gln Leu Phe Gln Phe Ser Ala Ser
             20                  25                  30

Asp Thr Ser Val Ile Phe Glu Glu Thr Asp Gly Glu Thr Val Leu Lys
         35                  40                  45

Ser Pro Ser Ile Tyr Glu Val Ile Lys Glu Ile Gly Glu Phe Ser Glu
     50                  55                  60

His His Phe Tyr Cys Ala Ile Phe Ile Pro Ser Thr Glu Asp His Ala
 65                  70                  75                  80

Tyr Gln Leu Glu Lys Lys Leu Ile Ser Val Asp Asp Asn Phe Arg Asn
                 85                  90                  95

Phe Gly Gly Phe Lys Ser Tyr Arg Leu Leu Arg Pro Ala Lys Gly Thr
            100                 105                 110
```

Thr Tyr Lys Ile Tyr Phe Gly Phe Ala Asp Arg His Ala Tyr Glu Asp
115 120 125

Phe Lys Gln Ser Asp Ala Phe Asn Asp His Phe Ser Lys Asp Ala Leu
130 135 140

Ser His Tyr Phe Gly Ser Ser Gly Gln His Ser Ser Tyr Phe Glu Arg
145 150 155 160

Tyr Leu Tyr Pro Ile Lys Glu
165

<210> SEQ ID NO 12
<211> LENGTH: 167
<212> TYPE: PRT
<213> ORGANISM: Staphylococcus sp.

<400> SEQUENCE: 12

Met Lys Lys Leu Tyr Thr Ser Tyr Gly Thr Tyr Gly Phe Leu His Gln
1 5 10 15

Ile Lys Ile Asn Asn Pro Thr His Gln Leu Phe Gln Phe Ser Ala Ser
20 25 30

Asp Thr Ser Val Ile Phe Glu Glu Thr Asp Gly Glu Thr Val Leu Lys
35 40 45

Ser Pro Ser Ile Tyr Glu Val Ile Lys Glu Ile Gly Glu Phe Ser Glu
50 55 60

His His Phe Tyr Cys Ala Ile Phe Ile Pro Ser Thr Glu Asp His Ala
65 70 75 80

Tyr Gln Leu Glu Lys Lys Leu Ile Ser Val Asp Asp Asn Phe Arg Asn
85 90 95

Phe Gly Gly Phe Lys Ser Tyr Arg Leu Leu Arg Pro Ala Lys Gly Thr
100 105 110

Thr Tyr Lys Ile Tyr Phe Gly Phe Ala Asp Arg His Ala Tyr Glu Asp
115 120 125

Phe Lys Gln Ser Asp Ala Phe Asn Asp His Phe Ser Lys Asp Ala Leu
130 135 140

Ser His Tyr Phe Gly Ser Ser Gly Gln His Ser Ser Tyr Phe Glu Arg
145 150 155 160

Tyr Leu Tyr Pro Ile Lys Glu
165

<210> SEQ ID NO 13
<211> LENGTH: 167
<212> TYPE: PRT
<213> ORGANISM: Staphylococcus sp.

<400> SEQUENCE: 13

Met Lys Lys Leu Tyr Thr Ser Tyr Gly Thr Tyr Gly Phe Leu His Gln
1 5 10 15

Ile Lys Ile Asn Asn Pro Thr His Gln Leu Phe Gln Phe Ser Ala Ser
20 25 30

Asp Thr Ser Val Ile Phe Glu Glu Thr Asp Gly Glu Thr Val Leu Lys
35 40 45

Ser Pro Ser Ile Tyr Glu Val Ile Lys Glu Ile Gly Glu Phe Ser Glu
50 55 60

His His Phe Tyr Cys Ala Ile Phe Ile Pro Ser Thr Glu Asp His Ala
65 70 75 80

Tyr Gln Leu Glu Lys Lys Leu Ile Ser Val Asp Asp Asn Phe Arg Asn
85 90 95

```
Phe Gly Gly Phe Lys Ser Tyr Arg Leu Leu Arg Pro Ala Lys Gly Thr
            100                 105                 110

Thr Tyr Lys Ile Tyr Phe Gly Phe Ala Asp Arg His Ala Tyr Glu Asp
        115                 120                 125

Phe Lys Gln Ser Asp Ala Phe Asn Asp His Phe Ser Lys Asp Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu
                165


<210> SEQ ID NO 14
<211> LENGTH: 167
<212> TYPE: PRT
<213> ORGANISM: Staphylococcus sp.

<400> SEQUENCE: 14

Met Lys Lys Leu Tyr Thr Ser Tyr Gly Thr Tyr Gly Phe Leu Asn Gln
  1               5                  10                  15

Ile Lys Ile Asn Asn Pro Ser His His Leu Phe Gln Phe Ser Thr Ala
            20                  25                  30

Asp Ser Ser Val Ile Phe Glu Glu Thr Glu Glu Asn Thr Val Leu Lys
        35                  40                  45

Ser Pro Ser Ile Tyr Glu Val Ile Lys Glu Ile Gly Ala Phe Asn Glu
     50                  55                  60

Asp His Phe Tyr Cys Ala Ile Phe Ile Pro Ser Thr Glu Asp His Val
 65                  70                  75                  80

Tyr Gln Leu Glu Lys Lys Leu Ile Ser Val Asp Asp Asn Phe Lys Asn
                85                  90                  95

Phe Gly Gly Phe Lys Ser Tyr Arg Leu Leu Arg Pro Val Lys Gly Thr
            100                 105                 110

Thr Tyr Lys Ile Tyr Phe Gly Phe Ala Asp Arg Gln Thr Tyr Glu Asp
        115                 120                 125

Phe Lys Asn Ser Asp Ala Phe Lys Asp His Phe Ser Lys Glu Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu
                165


<210> SEQ ID NO 15
<211> LENGTH: 167
<212> TYPE: PRT
<213> ORGANISM: Staphylococcus sp.

<400> SEQUENCE: 15

Met Lys Lys Leu Tyr Thr Ser Tyr Gly Thr Tyr Gly Phe Leu Asn Gln
  1               5                  10                  15

Ile Lys Ile Asn Asn Pro Ser His His Leu Phe Gln Phe Ser Thr Ala
            20                  25                  30

Asp Ser Ser Val Ile Phe Glu Glu Thr Glu Glu Asn Thr Val Leu Lys
        35                  40                  45

Ser Pro Ser Ile Tyr Glu Val Ile Lys Glu Ile Gly Ala Phe Asn Glu
     50                  55                  60

Asp His Phe Tyr Cys Ala Ile Phe Ile Pro Ser Thr Glu Asp His Val
 65                  70                  75                  80

Tyr Gln Leu Glu Lys Lys Leu Ile Ser Val Asp Asp Asn Phe Lys Asn
```

```
                85                  90                  95

Phe Gly Gly Phe Lys Ser Tyr Arg Leu Leu Arg Pro Val Lys Gly Thr
            100                 105                 110

Thr Tyr Lys Ile Tyr Phe Gly Phe Ala Asp Arg Gln Thr Tyr Glu Asp
        115                 120                 125

Phe Lys Asn Ser Asp Ala Phe Lys Asp His Phe Ser Lys Glu Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu
                165


<210> SEQ ID NO 16
<211> LENGTH: 176
<212> TYPE: PRT
<213> ORGANISM: Staphylococcus sp.

<400> SEQUENCE: 16

Met Lys Lys Leu Tyr Thr Ser Tyr Gly Thr Tyr Gly Phe Leu Asn Gln
  1               5                  10                  15

Ile Lys Ile Asn Asn Pro Ser His His Leu Phe Gln Phe Ser Thr Ala
            20                  25                  30

Asp Ser Ser Val Ile Phe Glu Glu Thr Glu Glu Lys Thr Val Leu Lys
        35                  40                  45

Ser Pro Ser Ile Tyr Glu Val Ile Lys Glu Ile Gly Ala Phe Asn Glu
    50                  55                  60

Asp His Phe Tyr Cys Ala Ile Phe Ile Pro Ser Thr Glu Asp His Val
 65                  70                  75                  80

Tyr Gln Leu Glu Lys Lys Leu Ile Ser Val Asp Asp Asn Phe Lys Asn
                85                  90                  95

Phe Gly Gly Phe Lys Ser Tyr Arg Leu Leu Arg Pro Val Lys Gly Thr
            100                 105                 110

Thr Tyr Lys Ile Tyr Phe Gly Phe Ala Asp Arg Gln Thr Tyr Glu Asp
        115                 120                 125

Phe Lys Asn Ser Asp Ala Phe Lys Asp His Phe Ser Lys Glu Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu Gly Ser Ser Ser Phe Met Val Gly Arg
                165                 170                 175


<210> SEQ ID NO 17
<211> LENGTH: 167
<212> TYPE: PRT
<213> ORGANISM: Staphylococcus sp.

<400> SEQUENCE: 17

Met Tyr Leu Tyr Thr Ser Tyr Gly Thr Tyr Gln Phe Leu Asn Gln Ile
  1               5                  10                  15

Lys Leu Asn His Gln Glu Arg Ser Leu Phe Gln Phe Ser Thr Asn Asp
            20                  25                  30

Ser Ser Ile Ile Leu Glu Glu Ser Glu Gly Lys Ser Ile Leu Lys His
        35                  40                  45

Pro Ser Ser Tyr Gln Val Ile Asp Ser Thr Gly Glu Phe Asn Glu His
    50                  55                  60

His Phe Tyr Ser Ala Ile Phe Val Pro Thr Ser Glu Asp His Arg Gln
 65                  70                  75                  80
```

```
Gln Leu Glu Lys Lys Leu Leu His Val Asp Val Pro Leu Ser Asn Phe
                85                  90                  95

Gly Gly Phe Lys Ser Tyr Arg Leu Leu Lys Pro Thr Glu Gly Ser Thr
            100                 105                 110

Tyr Lys Ile Tyr Phe Gly Phe Ala Asn Arg Thr Ala Tyr Glu Asp Phe
        115                 120                 125

Lys Ala Ser Asp Ile Phe Asn Glu Asn Phe Ser Lys Asp Ala Leu Ser
    130                 135                 140

Gln Tyr Phe Gly Ala Ser Gly Gln His Ser Ser Tyr Phe Glu Arg Tyr
145                 150                 155                 160

Leu Tyr Pro Ile Glu Asp His
                165


<210> SEQ ID NO 18
<211> LENGTH: 167
<212> TYPE: PRT
<213> ORGANISM: Staphylococcus aureus

<400> SEQUENCE: 18

Met Lys Lys Leu Tyr Thr Ser Tyr Gly Thr Tyr Gly Phe Leu His Gln
  1               5                  10                  15

Ile Lys Ile Asn Asn Pro Thr His Gln Leu Phe Gln Phe Ser Ala Ser
             20                  25                  30

Asp Thr Ser Val Ile Phe Glu Glu Thr Asp Gly Glu Thr Val Leu Lys
         35                  40                  45

Ser Pro Ser Ile Tyr Glu Val Ile Lys Glu Ile Gly Glu Phe Ser Glu
     50                  55                  60

His His Phe Tyr Cys Ala Ile Phe Ile Pro Ser Thr Glu Asp His Ala
 65                  70                  75                  80

Tyr Gln Leu Glu Lys Lys Leu Ile Ser Val Asp Asp Asn Phe Arg Asn
                85                  90                  95

Phe Gly Gly Phe Lys Ser Tyr Arg Leu Leu Arg Pro Ala Lys Gly Thr
            100                 105                 110

Thr Tyr Lys Ile Tyr Phe Gly Phe Ala Asp Arg His Ala Tyr Glu Asp
        115                 120                 125

Phe Lys Gln Ser Asp Ala Phe Asn Asp His Phe Ser Lys Asp Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu
                165


<210> SEQ ID NO 19
<211> LENGTH: 167
<212> TYPE: PRT
<213> ORGANISM: Listeria monocytogenes

<400> SEQUENCE: 19

Met Lys Lys Val Phe Ile Thr Thr Gly Thr Glu His Tyr Leu Arg Gln
  1               5                  10                  15

Leu Met Ala Asn Tyr Thr Gly Gly Asn Val Thr Leu Leu Gln Asn Phe
             20                  25                  30

Ser Gln Ser Leu Leu Tyr Gln Glu Ser Thr Gly Glu Lys Leu Phe Gln
         35                  40                  45

Glu Gly Ala Glu Tyr Arg Val Leu Gln Ser Ser Gly Ser Ile Lys Gly
     50                  55                  60
```

```
Phe Gly Val Val Val Phe Glu Tyr Ile His Leu Arg Asp Glu Glu Ile
 65                  70                  75                  80

Pro Ile Phe Leu Gln Met Tyr Gln Arg Ala Ser Leu His Phe Ser Glu
                 85                  90                  95

Thr Pro Gly Leu Gln Ser Thr Lys Leu Thr Lys Ala Met Asn Met Asn
            100                 105                 110

Lys Phe Leu Ile Ile Ser Phe Trp Asp Ser Glu Val Phe Phe His Asp
        115                 120                 125

Trp Lys Lys Ser Pro Leu Ser Lys Glu Ile Thr Asn Ile Met Arg Lys
    130                 135                 140

Asn Asn Thr Gln Ser Gly Phe Ser His Glu Asp Ile Tyr His Tyr Pro
145                 150                 155                 160

Glu Phe Ser His Asp Ala Lys
                165


<210> SEQ ID NO 20
<211> LENGTH: 166
<212> TYPE: PRT
<213> ORGANISM: Bacillus subtilis

<400> SEQUENCE: 20

Met Lys Val Tyr Ile Thr Tyr Gly Thr Ala Asp Phe Leu Lys Thr Ile
  1               5                  10                  15

Val Gln Lys His Pro Ser Glu Asn Ile Leu Leu Met Gln Gly Gln Glu
            20                  25                  30

Asn Ala Ile Leu Ile His Glu Thr Asn Gly Asp Thr Val Phe Gln Ala
        35                  40                  45

Pro His Ala Tyr Glu Val Ile Asp Gln Val Gly Glu Ile Lys His Pro
     50                  55                  60

Gly Phe Ala Val Leu Asn Asn Ile Ala Val Thr Gln Glu Gly Arg Pro
 65                  70                  75                  80

Leu Phe Glu Asn Arg Phe Lys Asn Arg Ala Gly Lys Val Glu Asn Glu
                 85                  90                  95

Pro Gly Phe Glu Ala Ile Arg Val Leu Arg Pro Leu Asp Ser Asp Thr
            100                 105                 110

Tyr Val Ile Leu Thr Leu Trp Glu Thr Glu Ser Ala Phe Gln Asp Trp
        115                 120                 125

Gln Gln Ser Gly Ser Tyr Lys Glu Ala His Lys Lys Arg Asp Thr Ser
    130                 135                 140

Ala Gly Ile Asp Thr Thr Ser Ile Phe Ser Arg Pro Ser Tyr Val Thr
145                 150                 155                 160

Thr Tyr Phe Ala Val Glu
                165


<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      formula peptide sequence
<220> FEATURE:
<221> NAME/KEY: MOD_RES
<222> LOCATION: (4)
<223> OTHER INFORMATION: Cys, Trp, Ile or a modified amino acid

<400> SEQUENCE: 21

Tyr Lys Pro Xaa Thr Asn Phe
  1               5
```

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic formula peptide sequence
<220> FEATURE:
<221> NAME/KEY: MOD_RES
<222> LOCATION: (4)
<223> OTHER INFORMATION: Cys, Trp, Ile or a modified amino acid

<400> SEQUENCE: 22

Tyr Ser Pro Xaa Thr Asn Phe
1 5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic formula peptide sequence
<220> FEATURE:
<221> NAME/KEY: MOD_RES
<222> LOCATION: (7)
<223> OTHER INFORMATION: Cys, Trp, Ile or a modified amino acid

<400> SEQUENCE: 23

Ile Lys Lys Tyr Lys Pro Xaa Thr Asn
1 5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic formula peptide sequence
<220> FEATURE:
<221> NAME/KEY: MOD_RES
<222> LOCATION: (7)
<223> OTHER INFORMATION: Cys, Trp, Ile or a modified amino acid

<400> SEQUENCE: 24

Ile Lys Lys Tyr Ser Pro Xaa Thr Asn
1 5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Tyr Lys Pro Ile Thr Asn
1 5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: may be c-term amidated

<400> SEQUENCE: 26

```
Tyr Ser Pro Trp Thr Asn Phe
  1               5


<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      formula peptide sequence
<220> FEATURE:
<221> NAME/KEY: MOD_RES
<222> LOCATION: (6)
<223> OTHER INFORMATION: Cys, Trp, Ile or a modified amino acid

<400> SEQUENCE: 27

Lys Lys Tyr Lys Pro Xaa Thr Asn
  1               5


<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      formula peptide sequence
<220> FEATURE:
<221> NAME/KEY: MOD_RES
<222> LOCATION: (6)
<223> OTHER INFORMATION: Cys, Trp, Ile or a modified amino acid

<400> SEQUENCE: 28

Lys Lys Tyr Ser Pro Xaa Thr Asn
  1               5


<210> SEQ ID NO 29
<211> LENGTH: 9
<212> TYPE: PRT
<213> ORGANISM: Staphylococcus aureus

<400> SEQUENCE: 29

Ile Lys Lys Tyr Lys Pro Ile Thr Asn
  1               5


<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

gaattccata tggctattaa aaagtataag                                      30


<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

cgcgcggatc cttatttttt cttacgtcca cg                                   32


<210> SEQ ID NO 32
<211> LENGTH: 7
```

-continued

```
<212> TYPE: PRT
<213> ORGANISM: Artificial Sequence
<220> FEATURE:
<223> OTHER INFORMATION: Description of Artificial Sequence: Synthetic
      RIP peptide analogue

<400> SEQUENCE: 32

Tyr Lys Pro Glu Thr Asn Phe
  1               5
```

METHODS AND COMPOSITIONS FOR THE TREATMENT AND PREVENTION OF *STAPHYLOCOCCUS* AND OTHER BACTERIAL INFECTIONS

CROSS REFERENCE TO RELATED APPLICATIONS

This application is a continuation of U.S. application Ser. No. 10/358,448, filed Feb. 3, 2003 and now issued as U.S. Pat. No. 7,323,179, which is a continuation-in-part of U.S. application Ser. No. 09/839,695, filed Apr. 19, 2001 and now issued as U.S. Pat. No. 7,067,135, which is a continuation-in-part of Ser. No. 09/054,331, filed Apr. 2, 1998 and now issued as U.S. Pat. No. 6,291,431, which claims the benefit of U.S. provisional application Ser. No. 60/068,094, filed Dec. 19, 1997, each of which is incorporated by reference in its entirety herein for all purposes.

TECHNICAL FIELD

The present invention relates to methods and compositions for treatment or prevention of bacterial biofilm, infection, diseases or symptoms caused by bacteria, including those associated with infection by *Staphylococcus* spp.

BACKGROUND OF THE INVENTION

Drug Resistant *Staphylococci* are a Major Medical Problem

*Staphylococci* (especially *S. aureus* and *S. epidermidis*) are major human pathogens and are the most common cause of nosocomial infections reported in the U.S. Each year approximately two million hospitalizations result in nosocomial infections, increasing hospital death rate in the U.S. by 35%. *S. aureus* and *S. epidermidis* infections are the leading cause of nosocomial pneumonia, surgical site and bloodstream infections, medical device associated infections, as well as community-acquired infections such as osteomyelitis and septic arthritis, skin infections, endocarditis, and meningitis (Rubin R. J. et al., Emerg. Infect. Dis. 1999; 5:9-17 [1]). Currently, more than 95% of patients with staphylococcal infections worldwide do not respond to first-line antibiotics such as penicillin or ampicillin. Drug-resistant *Staphylococcus* was once largely confined to hospitals and nursing homes but is now spreading to communities as well (Lowy F. D., *N. Engl. J. Med* 1998; 339:520-532 [2]). The emergence and spread of drug-resistant bacteria underscores the need to find new modes of prevention and alternative antibiotic treatment to bacterial infections, including *S. aureus, S. epidermidis* and others. The instant invention addresses this need and others.

*S. aureus* cause Diseases by Producing Virulence Factors

*S. aureus* are part of the normal flora of the human skin, but can cause fatal diseases due to the formation of biofilms and/or the production of toxic exomolecules. The toxins include toxic-shock syndrome toxin-1 (TSST-1), a pyrogenic toxin that causes toxic shock syndrome; staphylococcal enterotoxins, a major cause of food poisoning; proteases that allow the bacteria to exploit its environment of metabolites and enable its spread within the host; and hemolysins, leukocidin and other virulence factors that are expressed, secreted or sequestered by *Staphylococci* and have been shown to affect the outcome of the infective process [2].

A novel approach for therapy development is to interfere with staphylococcal virulence (biofilm formation and toxin production). Eliminating the production of virulence factors does not only make the bacteria far less pathogenic, but may also make the bacteria more susceptible to host immune defenses and to conventional antibiotics (Balaban N, et al., Science 1998; 280; 438-440 [3]).

Regulation of Staphylococcal Virulence by Quorum Sensing

Biofilm formation and toxin production is regulated by a quorum sensing mechanism, where molecules produced and secreted by the bacteria (autoinducers) reach a threshold concentration and activate signal transduction pathways, leading to activation of the genes that encode for virulence factors [2].

*S. aureus* express surface molecules such as fibronectin binding-proteins, fibrinogen binding-protein and protein A, in the early exponential phase of growth, when the bacteria are in lower density [2]. Expression of adhesion molecules allows the bacteria to adhere to and colonize host cells and implanted medical devices. When in higher densities, the bacteria produce toxic exomolecules such as Toxic Shock Syndrome Toxin-1 (TSST-1), enterotoxins, proteases and hemolysins that allow the bacteria to survive, disseminate and establish the infection [2].

The ability of the bacteria to express adhesion molecules and colonize when in lower densities and to express toxic exomolecules and cause disease when in higher densities, is due to a complex regulatory process, which involves quorum sensing (QS) mechanisms (Kleerebezem M., et al., Mol. Microbiol. 1997; 24: 895-904 [4]) and activation of genetic loci such as traP (Balaban N. et al., J Biol Chem 2001; 276:2658-2667 [5]) agr (Lina G., et al., Mol. Microbiol. 1998; 28-655-662 [6], sar (Heyer G., et al., Infect. Immun. 2002; 70:127-133 [7]), sae (Giraudo A. T. et al., FEMS Microbiol. Lett. 1999; 177:15-22 [8]). These processes act in parallel or in concert to regulate virulence [5].

To date, two staphylococcal quorum-sensing systems (SQS) have been described. SQS 1 consists of the autoinducer RNAIII-activating protein (RAP) and its target molecule TRAP [3, 5]. RAP is a protein of about 33 kDa [3] that is an ortholog of the ribosomal protein L2 (coded by the rplB gene) and usually consists of 277 amino acids. rplB is highly conserved among eubacteria (see detailed description below). TRAP is a ~2lkDa protein that is phosphorylated in the presence of RAP [5]. The sequence of TRAP is highly conserved among staphylococcal strains and species and its secondary structure is highly conserved among gram positive bacteria. TRAP usually consists of 167 amino acids (see detailed description below).

SQS 2 is composed of the products of the gene regulatory system agr. agr encodes two divergently transcribed transcripts, RNAII and RNAIII (Novick R. P., et al, *Mol. Gen. Genet.* 1995; 248: 446-458 [9], and Novick R. P. et al, *EMBO J.* 1993; 12:3967-3975 [10].) RNAII is a polycistronic transcript that encodes agrA, agrC, agrD and agrB, where agrD is a pro-peptide that yields an autoinducing peptide (AIP) that is processed and secreted with the aid of agrB (Otto M., *Peptides* 2001; 22:1603-1608[11] and Saenz H. L. et al., *Arch. Microbiol.* 2000; 174:452-455 [12]). Once agr is activated and AIP is secreted, it induces the phosphorylation of agrC [6] and agrA, leading to the production of the regulatory RNA molecule termed RNAIII [10]. RNAIII upregulates the production of numerous secreted toxins [10].

Interaction Between SQS 1 and SQS 2

RAP induces the phosphorylation of its target molecule TRAP, leading in a yet unknown manner both to increased cell adhesion and to the activation of agr. Once agr is activated and RNAII is produced (in the mid-exponential phase of growth), the octapeptide (AIP) and its receptor agrC are made. AIP downregulates TRAP phosphorylation [5] (leading to reduced adhesion properties) and independently to upregulation of the phosphorylation of its receptor agrC [6]. This leads to the phosphorylation of agrA, resulting in the production of RNAIII. RNAIII leads to the expression of many toxic exomolecules [10].

Inhibition of SOS 1: A Novel Mode of Therapy and Prevention of Bacterial Infections Mice that were vaccinated with RAP (native or recombinant) were protected from a challenge of *S. aureus [*3]. This confirms the important role of RAP in *S. aureus* pathogenesis and opens an opportunity for the development of a new vaccine.

Staphylococcal infections can be inhibited by RNAIII inhibiting peptide (RIP). RIP inhibits *Staphylococci* from adhering and from producing toxins by interfering with the known function of SQS 1. RIP competes with RAP on inducing TRAP phosphorylation, thus leading to inhibition of the phosphorylation of TRAP [5]. This leads to a decrease in cell adhesion and biofilm formation, to inhibition of RNAIII synthesis and to suppression of the virulence phenotype [3]. The peptide RIP was first isolated from culture supernatants of coagulase negative *Staphylococci* that were identified with 99% certainty to be *S. xylosus*. The sequence of RIP was identified as YSPXTNF (SEQ ID NO: 22), where X can be a Cys, a Trp, or a modified amino acid, as well as peptide derivatives like YKPITN (SEQ ID NO: 25) (Gov Y., et al., *Peptides,* 2001; 22:1609-1920 [13]. Synthetic RIP analogues were designed in their amide form as YSPWTNF(—NH2) (SEQ ID NO: 26) and shown to be extremely effective in inhibiting RNAIII in vitro and in suppressing *S. aureus* infections in vivo, including: cellulitis (tested in mice against *S. aureus* Smith Diffuse), septic arthritis (tested in mice against S. aureus LS-1), keratitis (tested in rabbits against *S. aureus* 8325-4), osteomyelitis (tested in rabbits against *S. aureus* MS), and mastitis (tested in cows against *S. aureus* Newbould 305, AE-1, and environmental infections) (Balaban N., et al., *Peptides* 2000; 21:1301 -1311 [14]. These findings indicate that RIP can serve as a useful therapeutic molecule to prevent and suppress staphylococcal infections.

Biofilm-related Infections

Bacteria that attach to surfaces aggregate in a hydrated polymeric matrix of their own synthesis to form biofilms. Formation of these sessile communities and their inherent resistance to antimicrobial agents are at the root of many persistent and chronic bacterial infections (Costerton J. W., et al., Science. 1999; 21:284:1318-1322 [15]). Biofilms develop preferentially on inert surfaces, or on dead tissue, and occur commonly on medical devices and fragments of dead tissue such as sequestra of dead bone; they can also form on living tissues, as in the case of endocarditis. Biofilms grow slowly, in one or more locations, and biofilm infections are often slow to produce overt symptoms. Sessile bacterial cells release antigens and stimulate the production of antibodies, but the antibodies are not effective in killing bacteria within biofilms and may cause immune complex damage to surrounding tissues. Even in individuals with excellent cellular and humoral immune reactions, biofilm infections are rarely resolved by the host defense mechanisms. Antibiotic therapy typically reverses the symptoms caused by planktonic cells released from the biofilm, but fails to kill the biofilm. For this reason biofilm infections typically show recurring symptoms, after cycles of antibiotic therapy, until the sessile population is surgically removed from the body. It is therefore important to prevent biofilm formation rather than to try to eradicate biofilms once they have formed.

As shown in Table 1, many of biofilm-related nosocomial infections are caused by *Staphylococci [*15].

TABLE 1

Partial list of human nosocomial infections involving biofilms.

| Infection or disease | Common biofilm bacterial species |
|---|---|
| Sutures | *S. aureus* and *Staphylococcus epidermidis* |
| Exit sites | *S. aureus* and *S. epidermidis* |
| Arteriovenous shunts | *S. aureus* and *S. epidermidis* |
| Schleral buckles | Gram-positive cocci |
| Contact lens | *P. aeruginosa* and Gram-positive cocci |
| Urinary catheter cystitis | *E. coli* and other Gram-negative rods |
| Peritoneal dialysis (CAPD) peritonitis | *Staphylococci*, variety of bacteria and fungi |
| Endotracheal tubes | a variety of bacteria and fungi |
| Hickman catheters | *S. epidermidis* and *C. albicans* |
| ICU pneumonia | Gram-negative rods |
| Central venous catheters | *S. epidermidis* and others |
| Mechanical heart valves | *S. aureus* and *S. epidermidis* |
| Vascular grafts | Gram-positive cocci |
| Orthopedic devices | *S. aureus* and *S. epidermidis* |
| Penile prostheses | *S. aureus* and *S. epidermidis* |

RIP Reduces Bacterial Adhesion

RIP decreased bacterial adhesion to eukaryotic cells (tested on HEp2 cells) and to plastic (tested on polystyrene, silicone and polyurethane (Balaban N., et al., *Kidney Int.* 2003; 63:340-345 [16]). RIP could be used to coat medical devices to prevent staphylococcal infections.

RIP Deviates from AIP

RIP deviates from AIP in that RIP is a linear peptide [13] while AIP must contain a thiolactone structure to be active [11], the sensor of RIP is TRAP [5] while the sensor of AIP is agrC [6], RIP inhibits both cell adhesion and toxin production [16] while inhibitory AIPs inhibit toxin production but activate cell adhesion (Vuong C., Saenz H. L., Gotz F., Otto M., Impact of the agr quorum-sensing system on adherence to polystyrene in *Staphylococcus aureus. J. Infect. Dis.* 2000; 182:1688-1693[17].

Molecular Mechanisms of RIP

While the specific molecular mechanisms are not fully understood, it is known that RIP inhibits agr expression (RNAII and RNAIII [13]) and therefore inhibits the production of toxins (Vieira-da-Motta O., et al., *Peptides,* 2001; 22:1621-1628 [18]). It is known that RIP regulates cell adhesion in an agr-independent mechanism, because adhesion of agr null cells is equally inhibited in the presence of RIP as the wild type [16]. Because RIP inhibits TRAP phosphorylation [5] and TRAP has been demonstrated to be essential for cell adhesion, agr expression and pathogenesis (see detailed description below), RIP regulates S. aureus pathogenesis via TRAP, and perhaps via additional targets.

The mechanism through which RIP inhibits quorum sensing mechanisms, discussed above, involves inhibition of the phosphorylation of TRAP. There is evidence of the presence of TRAP and TRAP phosphorylation in *S. epidermidis* (see detailed description below), indicating that there is a similar quorum sensing mechanisms both in *S. aureus* and in *S. epidermidis* and the potential for RIP to interfere with biofilm formation and infections caused by both species. In addition, there is evidence that TRAP is conserved among all staphylococcal strains and species, and thus that other staphylococcal species have a similar quorum sensing mechanism as described above. As a result, RIP should be effective against any type of *Staphylococcus*.

RAP and TRAP are Target Sites for Therapy in Many Types of Bacteria

Other infection-causing bacteria appear to have proteins with sequence similarity to TRAP. These bacteria include *Bacillus subtilus, Bacillus anthracis, Bacillus cereus, Listeria innocua, Listeria monoctogenes* (see detailed description of invention).

Still further, RAP is an ortholog of the ribosomal protein L2, encoded by the rplB gene. L2 is highly conserved among bacteria, including specifically *Streptococcus* ssp, *Listeria* spp, *Lactococcus*-spp, *Enterococcus* spp, *Escherichia coli, Clostridium acetobtylicum*, and *Bacillus* spp. This finding indicates that treatment aimed at disturbing the function of RAP in *S. aureus* will also be effective in treating L2-synthesizing bacteria as well (see detailed description).

SUMMARY OF THE INVENTION

The invention features methods and compositions for treatment and/or prevention of infection by, or disease caused by infection with bacteria expressing RAP or TRAP or RAP-like or TRAP-like molecules (for example *Staphylococcus* spp., including *S. aureus* and *S. epidermidis, Bacillus* spp., including *B. subtilus, B. cereus, B. anthracis, Listeria* spp., including *L. innocua* and *L. monoctogenes, Streptococcus pyogenes, Lactococcus lactis, Enterococcus faecalis, Escherichia coli*, and *Clostridium acetobtylicum*).

The invention features treatment methods including coating devices, injecting systemically (IV, IP, IM, or SQ), applying topically, or taking orally.

One aspect of the invention is a composition containing a polypeptide containing an amino acid sequence comprising all or parts of the general formula Y(K or S) PXTNF (SEQ ID NOS: 21 and 22), where any of the amino acids can be modified and where X can be C, W, or I. Pharmaceutical compositions are also provided in some embodiments.

A further aspect of the invention is a composition wherein the polypeptide comprises an amino acid sequence containing the general formula IKKY(K or S)PXTN (SEQ ID NOS: 23 and 24), where X is C, W, I, or modified amino acids. Pharmaceutical compositions are also provided in some embodiments.

A further aspect of the invention is a method for treating a host for certain bacterial infections, wherein an antagonist of the RAP receptor is administered to the host. In some embodiments the host is a human patient. In further embodiments the host is an animal, such as, but not limited to, an experimental animal. In some embodiments the antagonist is a polypeptide, a peptidomimetic, or an antibody.

A further aspect of the invention is a nucleic acid molecule encoding a polypeptide of the invention. The nucleic acid molecule can be RNA or DNA or an antisense nucleic acid molecule. In an embodiment, the nucleic acid molecule comprises the nucleotide sequence of RIP, RAP or TRAP or their homologues.

In another aspect, the invention features an isolated native or recombinant RAP polypeptide, as well as nucleic acid encoding such RAP polypeptides.

In another aspect, the invention features an isolated native or synthetic RIP peptide, as well as nucleic acid encoding such RIP peptides.

In another aspect, the invention features an isolated TRAP polypeptide (native or recombinant, TRAP or TRAP homologues), as well as nucleic acid encoding such TRAP polypeptides.

BRIEF DESCRIPTION OF THE FIGURES

FIG. 1 is a multi sequence alignment analysis (ClustalW) of deduced RAP rplB amino acid sequences from the following bacteria: *S. aureus* RN6390B (AF205220) (SEQ ID NO: 1), *S. epidermidis* RP62A (TIGR database) (SEQ ID NO: 2), *Streptococcus pyogenes* M1 GAS (AE014137) (SEQ ID NO: 6), *Listeria monocytogenes* EGD (AL591983) (SEQ ID NO: 3), *Lactococcus lactis* (AE006438) (SEQ ID NO: 7), *Enterococcus faecalis* (TIGR database) (SEQ ID NO: 5), *Escherichia coli* K12 (AE000408) (SEQ ID NO: 9), *Clostridium acetobutylicum* (AE007808) (SEQ ID NO: 8) and *Bacillus subtilis* (Z99104) (SEQ ID NO: 4).

FIG. 4 is a graph showing the percent mortality of Balb/c native mice (control) or mice vaccinated with rL2 and challenged with $2\times10^9$ *S. aureus.*

FIG. 5 is a graph showing the development of lesions in rL2 vaccinated animals that survived a challenge of $2\times10^9$ *S. aureus.*

FIG. 9 is a multi-sequence alignment analysis (ClustalW) of deduced TRAP amino acid sequences from staphylococcal strains and species (SEQ ID NOS: 10-17, respectively in order of appearance).

FIG. 15 is a table identified as Table 1. Prevention of *S. epidermidis* infection using RIP-coated Dacron grafts in the presence or absence of local (A) or parenteral (B) antibiotic prophylaxis.

FIG. 16 is a table identified as TABLE 2. RIP prevents Dacron-graft associate *S. epidermidis* (A) and *S. aureus* (B) infections.

DETAILED DESCRIPTION OF THE INVENTION

Figure 2:
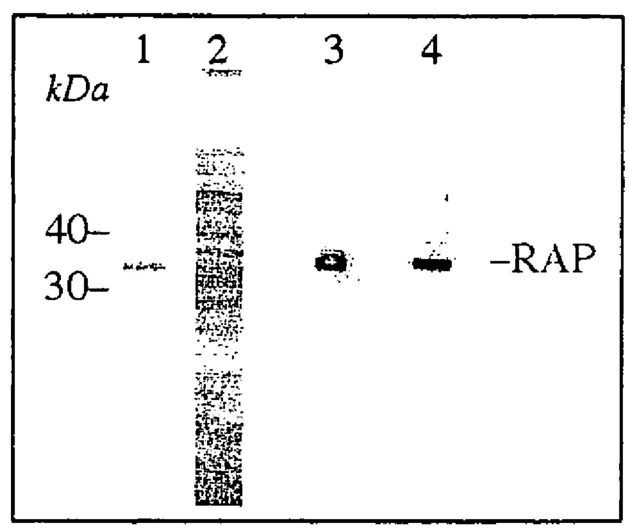
FIG. 2 is a photograph of a gel showing rRAP 2 μg (lanes 1,3) and culture supernatants of *S. aureus* RN6390B containing native RAP (30 μl of 30-fold concentration of post-exponential supernatant proteins) (lanes 2, 4) were applied to SDS 12.5% PAGE. Gel was western blotted, membrane stained in ponceau to visualize proteins (lanes 1, 2), blocked in milk, and incubated with monoclonal anti-rRAP antibodies (ascites, diluted 1:1000). Bound antibodies were detected by peroxidase-conjugated anti-mouse antibodies, visualized by chemiluminescence, and membrane autoradiographed (lanes 3, 4).

Before the present proteins, formulations and methods are described, it is to be understood that this invention is not limited to the particular compounds, characteristics and steps described, as such may, of course, vary. It is also to be understood that the terminology used herein is for the purpose of describing particular embodiments only, and is not intended to limit the scope of the present invention which will be limited only by the appended claims.

All publications and patents mentioned herein are incorporated herein by reference to disclose and describe the specific methods and/or materials in connection with which the publications and patents are cited. The publications and patents discussed herein are provided solely for their disclosure prior to the filing date of the present application. Nothing herein is to be construed as an admission that the present invention is not entitled to antedate such publication or patent by virtue of prior invention. Further, the dates of publication or issuance provided may be different from the actual dates which may need to be independently confirmed.

Generally, the nomenclature used hereafter, and the laboratory procedures in cell culture and protein biochemistry are those well known and commonly employed in the art. Generally, enzymatic reactions and column chromatography are performed according the manufacturer's specifications. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For the purposes of the present invention, the foregoing terms are defined below. The terms "pharmaceutically acceptable" and "therapeutically acceptable" refer to a substance which does not interfere with the effectiveness or the biological activity of the active ingredients and which is not toxic to the host or the patient.

The terms "encoding" or "encodes" refer generally to the sequence information being present in a translatable form, usually operably linked to a promoter. A sequence is operably linked to a promoter when the functional promoter enhances transcription or expression of that sequence. An anti-sense strand is considered to also encode the sequence, since the same informational content is present in a readily accessible form, especially when linked to a sequence which promotes expression of the sense strand. The information is convertible using the standard, or a modified, genetic code. See, e.g., Watson et al., (1987) *The Molecular Biology of the Gene*. (4th Edition), Vols. 1 & 2, Benjamin, Menlo Park, Calif.

As used to refer to nucleic acid sequences, the term "homologous" indicates that two or more nucleotide sequences share a majority of their sequence. Generally, this will be at least about 70% of their sequence and preferably at least 95% of their sequence.

Another indication that sequences are substantially identical is if they hybridize to the same nucleotide sequence under stringent conditions (see, e.g., Sambrook et al., *Molecular Cloning—A Laboratory Manual*, Cold Spring Harbor Laboratory, Cold Spring Harbor, N.Y., 1985). Stringent conditions are sequence-dependent and will be different in different circumstances. Generally, stringent conditions are selected to be about 5° C. lower than the thermal melting point ($T^A$ for the specific sequence at a defined ionic strength and pH. The $T_m$ is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

As used to refer to proteins, polypeptides, or peptides, which terms are used interchangeably herein, the term "homologous" is meant to indicate two proteins or polypeptides share a majority of their amino acid sequences. Generally, this will be at least 90% and usually more than about 95%. Homology for polypeptides or proteins is typically measured using sequence analysis software, see e.g., Sequence Analysis Software Package of the Genetics Computer Group, University of Wisconsin Biotechnology Center, 1710 University Avenue, Madison, Wis. 53705. Protein analysis software matches similar sequences using measure of homology assigned to various substitutions, deletions, and other modifications. Conservative substitutions typically include substitutions within the following groups: glycine, alanine; valine, isoleucine; leucine; aspartic acid, glutamic acid; asparagine, glutamine; serine, threonine; lysine, arginine; and phenylalanine, tyrosine.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

The term "isolated" as applied to, for example, nucleic acids, means a nucleic acid substantially separated from other macromolecules, cellular components, or DNA sequences which naturally accompany a native nucleic acid, e.g., ribosomes, polymerases, other nucleic acid sequences, and the like. The term includes a nucleic acid or polypeptide that has been removed from its naturally occurring environment, and includes recombinant or cloned DNA isolates and chemically synthesized analogues, and analogues biologically synthesized by heterologous systems. A substantially pure or biologically pure nucleic acid includes isolated forms of the nucleic acid.

The phrase "biologically pure" or "substantially pure" refers to material that is substantially or essentially free from components which normally accompany it as found in its native state, e.g., at least 60% free, preferably 75% free, and most preferably 90% free from other components with which it is naturally associated.

The term "recombinant" refers to a nucleic acid sequence which is not naturally occurring, or is made by the artificial combination of two otherwise separated segments of sequence, i.e., by chemical synthesis, genetic engineering, and the like.

The term "treatment" or "treating" means any therapeutic intervention in a mammal, preferably a human or bovine, or any other animal capable of suffering from a bacterial infection of a type that could be prevented and/or treated as described herein. The range of such animals is considered to be quite broad, and includes species as disparate as humans and birds.

(i) prevention, that is, causing the clinical symptoms not to develop, e.g., preventing infection from occurring and/or developing to a harmful state;

(ii) inhibition, that is, arresting the development of clinical symptoms, e.g., stopping an ongoing infection so that the infection is eliminated completely or to the degree that it is no longer harmful;

(iii) relief, that is, causing the regression of clinical symptoms, e.g., causing a relief of fever and/or inflammation caused by an infection; and (iv) in prevention of biofilm formation (or microbiological evidence of bacteria (prior to actual symptoms)).

Treatment is generally applied to any mammal susceptible to of having a[n] bacterial infection caused by any of the species described herein (e.g., mammals, birds, etc.), generally a mammal, for example a human or bovine where the treatment can be applied for prevention of bacterial infection or for amelioration of active bacterial infection, where the bacteria is a *Staphylococcus* spp bacteria.

The terms "effective amount" and/or "therapeutic amount" mean a dosage sufficient to provide prevention and/or treatment for the disease state being treated. This will vary depending on the patient, the disease and the treatment being effected. In the case of a bacterial infection, an "effective amount" is that amount necessary to substantially improve the likelihood of treating the infection, in particular that amount which improves the likelihood of successfully preventing infection or eliminating infection when it has occurred.

The term "protein" "polypeptide" or "peptide" as used herein is intended to encompass any amino acid sequence and include modified sequences (e.g. glycosylated, PEGylated, containing conservative amino acid substitutions, containing protective groups including for example 5-oxo-prolyl, amidation, etc.). The term includes naturally occurring (e.g., non-recombinant) proteins, polypeptides, peptides, and oligopeptides, as well as those which are recombinantly or synthetically synthesized according to methods well known in the art. As used in connection with the present invention the term "protein" "polypeptide" or "peptide" is specifically intended to cover naturally occurring molecules which occur in *Staphylococcus* spp. and useful in treating infection or in generating antibodies useful in treating infection. Where "polypeptide" "protein" or "peptide" are recited herein to refer to an amino acid sequence of a naturally-occurring protein molecule, "polypeptide" "protein," or "peptide", and like terms are not meant to limit the amino acid sequence to the complete, native amino acid sequence associated with the recited protein molecule. In addition, the polypeptides and proteins of the invention, or fragments thereof, can be generated in synthetic form having D-amino acids rather than the naturally occurring L-amino acids.

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g., a RIP, TRAP or RAP protein-encoding polynucleotide or a RIP derivative, TRAP-like or RAP-like protein-encoding polynucleotide)), "polynucleotide" is meant to encompass polynucleotides that encode a protein that is functionally equivalent to the recited protein, e.g., polynucleotides that are degenerate variants (i.e., variants in nucleic acid sequence that encode the same amino acid sequence and exist due to the degeneracy of the genetic code), or polynucleotides that encode biologically active variants or fragments of the recited protein.

By "antisense polynucleotide" is meant a polynucleotide having a nucleotide sequence complementary to a given polynucleotide sequence including polynucleotide sequences associated with the transcription or translation of the given polynucleotide sequence, (e.g., a promoter) and/or to a coding sequence of the given polynucleotide sequence, where the antisense polynucleotide is capable of hybridizing to a polynucleotide sequence. Of particular interest are antisense polynucleotides capable of inhibiting transcription and/or translation, either in vitro or in vivo.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen et al. 1993, Anticancer Drug Des. 8:53-63).

The term "antibody" is meant to refer to an immunoglobulin protein that is capable of binding an antigen. "Antibody" as used herein is meant to include the entire antibody as well as any antibody fragments (e.g., F(ab)', Fab, Fv) capable of binding the epitope, antigen or antigenic fragment of interest. Preferred antibodies for assays and vaccines of the invention are immunoreactive or immunospecific for and therefore specifically and selectively bind to a protein of interest, e.g., an anti-RAP or TRAP antibody. The term "antibody" encompasses all types of antibodies e.g., polyclonal, monoclonal, humanized, chimeric, and those produced by the phage display methodology. Particularly preferred antibodies of the invention are antibodies which have a relatively high degree of affinity for RAP or TRAP. An antibody of the invention is preferably immunoreactive with and immunospecific for a specific species, e.g., RAP or TRAP obtained from *Staphylococcus aureus*.

"Antigenic fragment" of a protein is meant a portion of such a protein which is capable of binding an antibody.

By "binds specifically" is meant high avidity and/or high affinity binding of an antibody to a specific polypeptide, e.g., epitope of a protein, e.g., RAP protein. Antibody binding to its epitope on this specific polypeptide is preferably stronger than binding of the same antibody to any other epitope, particularly those which may be present in molecules in association with, or in the same sample, as the specific polypeptide of interest, e.g., binds more strongly to epitope fragments of a protein such as RAP so that by adjusting binding conditions the antibody binds almost exclusively to an epitope site or fragments of a desired protein.

By "detectably labeled antibody" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art include radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. *Antibodies: A Laboratory Manual* (1988) Cold Spring Harbor Laboratory Press, Cold Spring Harbor, N.Y.)).

The instant invention provides polypeptides for the prevention and treatment of infections caused by *Staphylococcus* spp. and other bacteria. These polypeptides contain the general formula Y(K or S)PXTNF (SEQ ID NOS: 21 and 22), where X is C, W, or I. Amino acids can be modified and can include D-amino acids. In a further embodiment, the polypeptides may contain the general formula KKY(K or S) PXTN (SEQ ID NOS: 27 and 28), where X is C, W, or I, or modified amino acids.

The use of nucleic acids encoding the polypeptides of the invention is also included in the scope of the invention. Such nucleic acids may be DNA, RNA, or antisense nucleic acids. The nucleic acid molecules of the invention may be provided as synthetic or purified, isolated molecules, including but not limited to "naked DNA"; in vectors such as but not limited to plasmids or viruses, including expression vectors, or complexed to other compounds for administration. Such techniques are well known in the art. The polypeptides of the invention are preferably synthesized de novo by any technique commonly known in the art or may be encoded by nucleic acid, such as RNA or DNA, delivered to the host.

The polypeptides of the invention are typically administered to hosts having or at risk of having a staphylococcal infection such as an *S. aureus* or *S. epidermidis* infection. The hosts are typically human patients. Animals may also be treated with the compositions of the invention, including but not limited to animals of commercial or veterinary importance such as cows, sheep, goats, rabbits and pigs, and experimental animals such as rats, mice, rabbits or guinea pigs.

As used herein, "therapeutic dose" is a dose that prevents, alleviates, abates, or otherwise reduces the severity of symptoms in a patient. The compositions of the invention may be used prophylactically to prevent staphylococcal infections or may be therapeutically used after the onset of symptoms. In some embodiments, induction of the formation of antibodies to the administered compound is desirable. In such instances, standard immunization protocols used in the art are preferred. The compositions administered for immunization may optionally include adjuvants.

In some embodiments of the invention, antagonists of RAP or TRAP or RAP receptor are provided. Without being limited to any one theory, RIP may function by competing with RAP for binding to the RAP receptor, thus acting as an antagonist of the RAP, TRAP and/or RAP receptor. Such antagonists include but are not limited to antibodies that specifically bind to RAP, or TRAP; antibodies that specifically bind to a RAP or TRAP ligand; ligands for RAP, TRAP or RIP; antisense nucleic acids; and peptide, non-peptide, and peptidomimetic analogs of RAP, RIP, and their ligands.

Antibodies can be synthetic, monoclonal, or polyclonal and can be made by techniques well known in the art. For therapeutic applications, "human" monoclonal antibodies having human constant and variable regions are often preferred so as to minimize the immune response of a patient against the antibody. Such antibodies can be generated by immunizing transgenic animals that contain human immunoglobulin genes. See Jakobovits et al., *Ann. N.Y. Acad. Sci.* 764:525-535 (1995). In connection with synthetic and semi-synthetic antibodies, such terms are intended to cover but are not limited to antibody fragments, isotype switched antibodies, humanized antibodies (e.g., mouse-human, human-mouse, and the like), hybrids, antibodies having plural specificities, fully synthetic antibody-like molecules, and the like.

As discussed below, antibodies can be screened for the ability to block the binding of a ligand to RAP, TRAP or RIP and/or for other properties, such as the ability to protect in vivo against bacterial infection.

In some embodiments of the invention, antisense nucleic acid molecules are used as antagonists of RAP or TRAP. Antisense nucleic acid molecules are complementary oligonucleotide strands of nucleic acids designed to bind to a specific sequence of nucleotides to inhibit production of a targeted protein. These agents may be used alone or in combination with other antagonists.

The antisense antagonist may be provided as an antisense oligonucleotide, such as RNA (see, for example, Murayama et al,. *Antisense Nucleic Acid Drug Dev.* 7:109-114 ((1997)). Antisense sequences may also be provided in a viral vector, such as, for example, in hepatitis B virus (see, for example, Ji et al., *J. Viral Hepat.* 4:167-173 (1997)); in adeno-associated virus (see, for example, Xiao et al., *Brain Res.* 756:76-83

(1997)); or in other systems including, but not limited to, an HVJ(Sendai virus)-liposome gene delivery system (see, for example, Kaneda et al, *Ann. N.Y. Acad. Sci.* 811:299-308 (1997)); a "peptide vector" (see, for example, Vidal et al., *CR Acad. Sci IU*32):279-287 (1997)); as a gene in an episomal or plasmid vector (see, for example, Cooper et al., *Proc. Natl. Acad. Sci. US.A.* 94:6450-6455 (1997), Yew et al., *Hum. Gene Ther.* 8:575-584 (1997)); as a gene in a peptide-DNA aggregate (see, for example, Niidome et al., *J. Biol. Chem.* 272: 1530.7-15312 (1997)); as "naked DNA" (see, for example, U.S. Pat. No. 5,580,859 and U.S. Pat. No. 5,589,466); and in lipidic vector systems (see, for example, Lee et al., *Crit. Rev. Ther. Drug Carrier Syst.* 14:173-206 (1997)).

Candidate antagonists of the RAP, TRAP or RAP receptor can be screened for function by a variety of techniques known in the art and/or disclosed within the instant application, such as protection against S. aureus infection in a mouse model. A multitude of appropriate formulations of the antagonists of the invention can be found in the formulary known to all pharmaceutical chemists: *Remington's Pharmaceutical Sciences*, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in Goodman and Gilman's, *The Pharmacological Basis of Therapeutics,* 7th Edition (1985), MacMillan Publishing Company, New York, and Remington's *Pharmaceutical Sciences* 18th Edition, (1990), Mack Publishing Co., Easton Pa. Methods for administration are discussed therein, including oral, intravenous, intraperitoneal, intramuscular, transdermal, nasal, iontophoretic administration, and the like.

The compositions of the invention may be administered in a variety of unit dosage forms depending on the method of administration. For example, unit dosage forms suitable for oral administration include solid dosage forms such as powder, tablets, pills, and capsules, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like.

Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as an antibody, or with other therapeutic or immunogenic compositions. Thus, liposomes either filled or decorated with a desired composition of the invention can be delivered systemically, or can be directed to a tissue of interest, where the liposomes then deliver the selected therapeutic/immunogenic polypeptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szokaet et al., *Ann. Rev. Biophys. Bioeng.* 9:467 (1980), U.S. Pat. Nos. 4,235,871, 4,501,728, 4,837,028, and 5,019,369, incorporated herein by reference.

A liposome suspension containing a composition of the invention may be administered intravenously, locally, topically, etc. in a dose which varies according to, inter alia, the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more compositions of the invention, and more preferably at a concentration of 25%-75%.

For aerosol administration, the compositions of the invention are preferably supplied in finely divided form along with a surfactant and propellant. Typical percentages of compositions of the invention are 0.01%-20% by weight, preferably 1%-10%. The surfactant must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included, as desired, as with, e.g., lecithin for intranasal delivery.

The constructs of the invention can additionally be delivered in a depot-type system, an encapsulated form, or an implant by techniques well-known in the art. Similarly, the constructs can be delivered via a pump to a tissue of interest.

Any of the foregoing formulations may be appropriate in treatments and therapies in accordance with the present invention, provided that the active agent in the formulation is not inactivated by the formulation and the formulation is physiologically compatible. Polyclonal and/or monoclonal antibodies to the polypeptides of the present invention may be prepared. The polypeptides of the invention thereof may be prepared as described herein, and coupled to a carrier molecule, for example keyhole limpet hemocyanin, and injected into rabbits at selected times over several months. The rabbit sera may be tested for immunoreactivity to the polypeptides thereof. Monoclonal antibodies may be made by injecting mice with the polypeptides. Monoclonal antibodies may be screened by methods known in the art, as are described, for example, in Harlow and Lane (1988) *Antibodies: A laboratory manual*. Cold Spring Harbor Press, New York, and Coding (1986) *Monoclonal antibodies: Principles and Practice* (2d ed.) Academic Press, New York. The antibodies will be tested for specific immunoreactivity with an epitope of the polypeptides. These antibodies will find use in diagnostic assays or as an active ingredient in a pharmaceutical composition.

For production of polyclonal antibodies, an appropriate target immune system is selected, typically a mouse or rabbit, although other species such as goats, sheep, cows, guinea pigs, and rats may be used. The substantially purified antigen is presented to the immune system according to methods known in the art. The immunological response is typically assayed by an immunoassay. Suitable examples include ELISA, RIA, fluorescent assay, or the like. These antibodies will find use in diagnostic assays or as an active ingredient in a pharmaceutical composition.

RAP Nucleic Acid and Proteins

The present invention also provides a protein (RAP) isolated and purified from a non-pathogenic Staphylococcus spp. The RAP protein has a molecular weight of about 33 kDa. In one embodiment, RAP is the protein encoded by a polynucleotide comprising the sequence of SEQ ID NO: 12, and comprising an amino acid sequence of SEQ ID NO: 13. These sequences are provided in the Sequence Listing below.

RAP Nucleic Acid

The term "RAP gene" is used generically to designate RAP genes and their alternate forms. "RAP gene" is also intended to mean the open reading frame encoding specific RAP proteins, and adjacent 5' and 3' non-coding nucleotide sequences involved in the regulation of expression (e.g., promoter region). The gene may be introduced into an appropriate vector for extrachromosomal maintenance or for integration into the host. In one embodiment the RAP gene comprises the sequence of SEQ ID NO: 12.

RAP regulatory sequences may be used to identify cis acting sequences required for transcriptional or translational regulation of RAP expression, especially at different stages of growth (e.g., early, mid, and late log phase), and to identify cis acting sequences and trans acting factors that regulate or mediate RAP expression. Such transcriptional or translational control regions may be operably linked to a RAP coding sequence or other coding sequence.

The nucleic acid compositions used in the subject invention may encode all or a part of the RAP protein as appropriate. Fragments may be. obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e., greater than 100 nt are useful for production of the encoded polypeptide. For use in amplification reactions, such as PCR, a pair of primers will be used.

The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The RAP gene and RAP coding sequence are isolated and obtained in substantial purity, generally as other than an intact bacterial chromosome. Usually, the DNA will be obtained substantially free of other nucleic acid sequences that do not include a RAP sequence or fragment thereof, generally being at least 50%, usually at least 90% pure and are typically "recombinant", i.e., flanked by one or more nucleotides with which it is not normally associated on a naturally occurring chromosome.

The DNA sequences are used in a variety of ways. They may be used as probes for identifying RAP coding sequences of other strains of *Staphylococcus* or of other bacteria. Homologues isolated from other strains, species, or genera generally have substantial sequence similarity to one another, i.e., at least 75%, usually at least 90%, more usually at least 95% sequence identity. In general, RAP-encoding sequences of the invention (including homologues, variants, etc.), are characterized by having a sequence identity greater than at least about 65%, preferably at least about 75%, more preferably at least about 85%, and can be greater than at least about 90% or more as determined by the Smith-Waterman homology search algorithm as implemented in MPSRCH program (Oxford Molecular). For the purposes of this invention, a sequence identity is calculated using the Smith-Waterman algorithm as follows: Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

Nucleic acids having sequence similarity can also be detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). In addition, sequence identity may also be determined by hybridization under high stringency conditions, for example, at 50° C. or higher and 0.1×SSC (15 mM Saline/0.15 mM sodium citrate). By using probes, particularly labeled probes of DNA sequences, one can isolate homologous or related genes. It may also be possible to identify homologues of RAP from mammalian sources.

The RAP-encoding DNA may also be used to detect expression of the gene in a biological specimen. Methods and materials for probing a sample for the presence of particular nucleotide sequences are well established in the literature and do not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to an RAP sequence is indicative of RAP gene expression in the sample.

The RAP nucleic acid sequence may be modified for a number of purposes, particularly where they will be used intracellularly, for example, by being joined to a nucleic acid cleaving agent, e.g., a chelated metal ion, such as iron or chromium for cleavage of the gene; or the like.

The RAP coding sequence and/or promoter sequence may be mutated in various ways known in the art to generate targeted changes in promoter strength, sequence of the encoded protein, etc. The DNA sequence or product of such a mutation will be substantially similar to the sequences provided herein, i.e., will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain. Other modifications of interest include production of fusion proteins (e.g., with green fluorescent proteins (GFP), luciferase, and the like).

Techniques for in vitro mutagenesis of cloned genes are known. Examples of protocols for scanning mutations may be found in Gustin et al., 1993 *Biotechniques* 14:22; Barany, 1985 *Gene* 37:111-23; Colicelli et al., 1985 *Mol. Gen. Genet.* 199:537-9; and Prentki et al., 1984 *Gene* 29:303-13. Methods for site specific mutagenesis can be found in Sambrook et al., 1989 *Molecular Cloning. A Laboratory Manual*, CSH Press, pp. 15.3-15.108; Weiner et al., 1993 *Gene* 126:35-41; Sayers et al., 1992 *Biotechniques* 13:592-6; Jones and Winistorfer, 1992 *Biotechniques* 12:528-30; Barton et al., 1990 *Nucleic Acids Res.* 18:7349-55; Marotti and Tomich, 1989 *Gene Anal. Tech.* 6:67-70; and Zhu 1989 *Anal. Biochem.* 177:120-4.

RAP Protein

RAP protein can be produced by any suitable means, e.g., by isolation from a bacteria that naturally expresses RAP, by recombinant means (e.g., by expression of a polynucleotide having a sequence of SEQ ID NO: 12), by synthetic means, and the like.

In one embodiment, RAP is isolated directly from a strain of *Staphylococcus* producing RAP, e.g., *S. aureus*. Typically, wild type cells are collected from post-exponential culture broth. Cells are then centrifuged and the supernatant subjected to purification by, for example, filtration followed by lyophilization, resuspension in water, and further purification.

The *Staphylococci* bacterium from which RAP may be isolated may include, but is not necessarily limited to, *S. aureus, S. capitus, S. warner, S. capitis, S. caprae, S. carnosus, S. saprophyticus, S. chronii, S. simulans, S. caseolyticus, S. epidermidis, S. haemolyticus, S. hominis, S. hyicus, S. kloosii, S. lentus, S.lugdunensis, S. scruri, S. simulans*, and *S. xylosus*. Preferably RAP is isolated from *S. aureus*.

In another embodiment, RAP-encoding nucleic acid is employed to synthesize full-length RAP protein or fragments thereof, particularly fragments corresponding to functional domains (e.g., phosphorylation sites that interact with RAP, etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae,* or cells of a higher organism such as vertebrates, particularly mammals, e.g., COS-7 cells, may be used as the expression host cells. Alternatively, RAP fragments can be synthesized.

With the availability of the polypeptides in large amounts, by employing an expression host, RAP protein can be isolated and purified in accordance with conventional ways, e.g., using HPLC, exclusion chromatography, gel electrophoresis, affinity chromatography, or other purification technique. The purified protein will generally be at least about 80% pure, preferably at least about 90% pure, and may be up to and including 100% pure.

The RAP proteins (native, recombinant or synthetic) can be used for the production of antibodies, where short fragments provide for antibodies specific for the particular polypeptide, and larger fragments or the entire protein allow for the production of antibodies over the surface of the polypeptide. Antibodies may be raised to the wild-type or variant forms of RAP. Antibodies may be raised to isolated peptides corresponding to these domains, or to the native protein, e.g., by immunization with cells expressing RAP, immunization with liposomes having RAP protein inserted in the membrane, etc.

Anti-RAP Antibodies

The present invention also provides an antibody that specifically binds and is immunoreactive with RAP. The antibody may be monoclonal, polyclonal or humanized, and is prepared using methods well known in the art. In general, antibodies are prepared in accordance with conventional ways, where the protein or an antigenic portion thereof is used as an immunogen, by itself or conjugated to known immunogenic carriers, e.g., KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. In a preferred embodiment, the spleen or lymph node cells and myeloma cells are mixed in about 20:1 to about 1:1 ratio, but preferably in about 2:1 ratio. It is preferred that the same species of animal serve as the source of somatic and myeloma cells used in the fusion procedure, where the animal is chosen from rat, mouse, rabbit, cow, chicken, turkey, or man. The fusion of the somatic and myeloma cells produces a hybridoma, which is grown in culture to produce the desired monoclonal antibody by standard procedures. For further description, see, for example, *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage "display" libraries, usually in conjunction with in vitro affinity maturation.

The polyclonal antibodies of the present invention may be produced by injecting a rat, a mouse, a rabbit, a cow, a chicken, or a turkey with RAP to initiate an immunogenic response. They can be polyclonal or monoclonal, and can be engineered or synthesized. RAP may be coupled to a protein carrier such as keyhole limpet hemocyanin (KLH) or bovine serum albumin (BSA). An adjuvant may also be used. After a suitable amount of time to establish a high-titer of anti-RAP antibodies, the serum or eggs are collected. The presence of antibody in the serum or eggs may be tested by radioimmunoassay (RIA), by enzyme-linked immunosorbent assay (ELISA), or by immunoprecipitation. The immunoglobulins may be isolated by the sequential precipitation methods, by conventional methods of "salting out" the protein fractions from a salt solution, or by chromatographic methods well known to those skilled in the art.

RAP

RAP rplB Sequences in Bacteria

RAP was purified from culture supernatants of S. aureus RN6390B, and the $NH_2$ terminal sequence of RAP was determined to be IKKYKPITN (SEQ ID NO: 29) (Balaban N., et al., Science 2000, 287:391a [18]). This sequence was compared (TBLASTN algorithm) to several *S. aureus* databases where only one ORF was found to match strongly to the above peptide sequence. This ORF encodes a putative 277 amino acid protein, which is an ortholog of L2 or rplB sequences (Balaban N., et al., Science 2000, 289:905-920 [19]).

The corresponding gene in *S. aureus* RN6390B was amplified by PCR and sequenced (GenBank accession number AF205220). *S. aureus* putative rplB is highly homologous to rplB in other bacteria (FIG. 1). Furthermore, its sequence was compared to that of other *S. aureus* genome sequences available, and it was found to be totally conserved among strains (data not shown).

Production of Recombinant RAP (Termed Either rRAP or rL2)

To produce rRAP, forward and reverse primers corresponding to 5' and 3' ends of rap (rplB) gene with added restriction sites were designed. These primers were used to amplify the complete rplB gene by PCR, using *S. aureus* RN6390B chromosomal DNA as a template. Amplified DNA was digested and ligated into the corresponding sites of pET14b vector (Novagen, Wis.) which possesses a six histidine tag at the 5' end of the inserted gene. Plasmid containing rap (pET2-5) was used to transform *E. coli* BL-21(DE3)/pLysS. Cells were induced and harvested, and recombinant His-rRAP protein was isolated using a nickel column and the His-tag was removed by thrombin.

Specifically, to produce rL2, forward and reverse primers corresponding to the 5' and 3' ends of rap gene with added 5' NdeI and 3' BamHI restriction sites were designed based on the sequence of rap (underlined). These primers, 5' GAATTCCATATGGCTATTAAAAAGTATAAG 3' (nucleotides 1-21 (SEQ ID NO: 30)) and 5' CGC GCG GAT CCTTATTTTTTCTTACGTCCACG 3' (complement of nucleotides 840-819 (SEQ ID NO: 31), were used to amplify the complete rap gene by PCR, using *S. aureus* chromosomal DNA as a template. Amplified DNA was digested by NdeI and BamHI and ligated into the corresponding sites of pETl4b vector (Novagen, Wis.) which possesses a six histidine tag at the 5' end of the inserted gene. Plasmid containing rap (pET2-5) was used to transform *E. coli* BL-2 1 (DE3) pLysS (SBpET2-5). Induction of synthesis of recombinant protein was carried out by addition of 1 mM IPTG to the culture and incubation for 3 hours. Cells were harvested and washed once with 50 mM Tris buffer pH 7.9. Recombinant His-rRAP protein was isolated using a nickel column according to the manufacturer's instructions with some modifications (Xpress Systems Protein Purification, Invitrogen, Calif.). Cell pellet of 50 ml was resuspended in 10 ml binding buffer (20 mM sodium phosphate pH 7.8, 0.5M NaCl) and sonicated (for 2 cycles of 15 sec pulses at the maximal level with 30 sec intervals) and then spun in a microcentrifuge. The supernatant was loaded onto the pre-equilibrated nickel column. Prior to loading, the column containing chelated Sepharose beads was loaded with a charging buffer containing 50 mM NiCl, and equilibrated with binding buffer. The column was washed three times with five volumes of binding buffer, followed by three washes with five volumes of 20 mM sodium phosphate, 0.5M NaCl, pH 7.8, then with buffer adjusted to pH 6. Recombinant protein was sequentially eluted from the column using 0-5M imidazole. The His-tag was removed by thrombin.

Monoclonal Anti-rRAP Antibodies Recognize Native RAP

Monoclonal antibodies were produced from mice that were primed by rRAP. Hybridoma supernatants were tested by ELISA for the presence of specific antibodies against injected antigen. Positive hybridomas were cloned and used to raise ascites. To test if antibodies to recombinant protein recognize the native molecule, rRAP and partially purified native RAP (post-exponential supernatants of wild type *S. aureus* RN6390>10 kDa) were applied to SDS 12.5% PAGE, western blotted, and membrane stained in ponceau (FIG. 2, lanes 1, 2). The membrane was blocked, and incubated with ascites made of a positive anti-rRAP hybridoma (diluted 1:1000). Bound antibody was detected using peroxidase-conjugated anti-mouse IgG, and visualized by chemiluminescence (FIG. 2, lanes 3, 4). As shown in FIG. 2, monoclonal antibodies raised against rRAP specifically recognize the native molecule that is secreted to the supernatant (FIG. 2, lane 4).

Recombinant RAP is Active and Induces RNAIII Synthesis

Figure 3A:
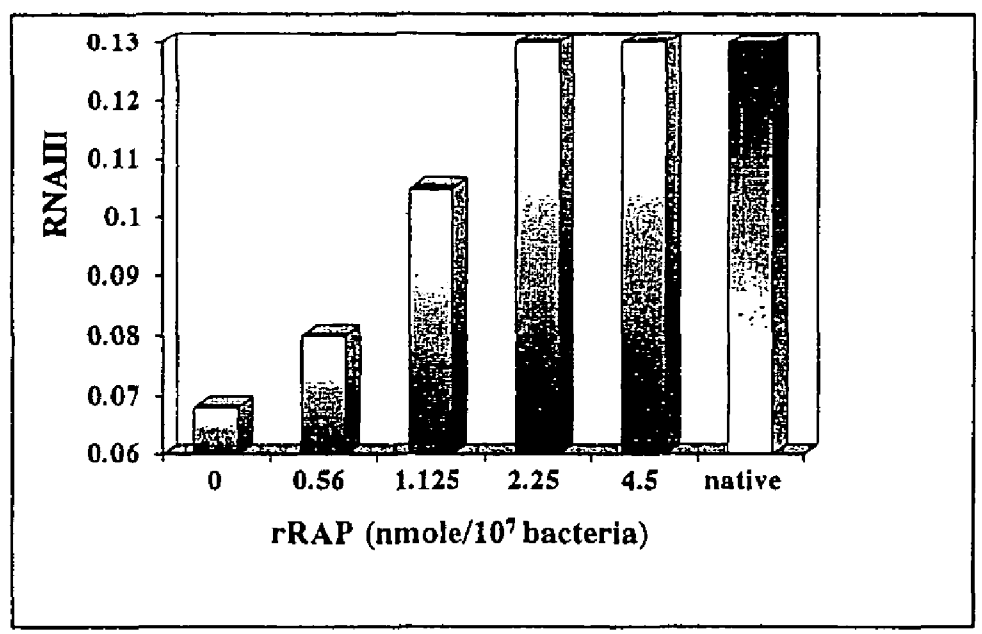
FIG. 3A is a graph showing that S. aureus cells containing the rnaiii:. blaZ fusion construct ($2\times10^7$ early exponential) were grown for 45 min with increasing amounts of rRAP (0-100 μg). β-lactamase activity was determined and expressed as OD at 490/650 nm. As a positive control, partially purified RAP (native, post-exponential supernatants of *S. aureus* RN6390B>10 kDa that were applied to a 10 kD cutoff membrane).
Figure 3B:
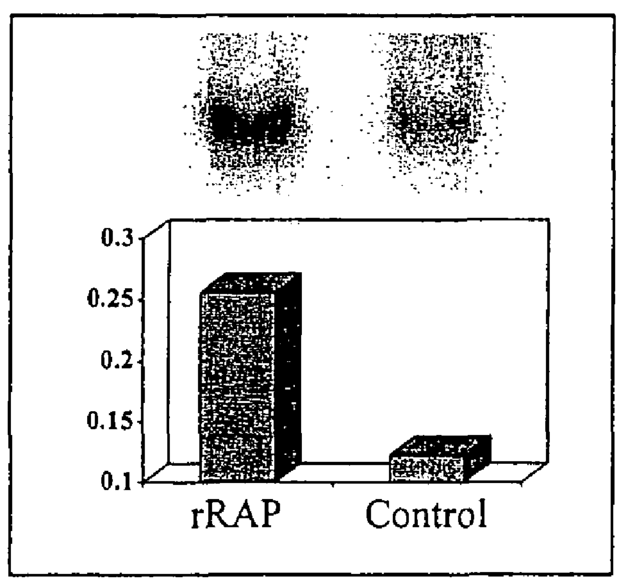
FIG. 3B is a photograph of a gel showing that cells ($10^8$ early exponential) were grown with (lane 1) or without (lane 2) 1 mg rRAP for 30 min, cells were collected, Northern blotted, and the presence of RNAIII was detected using RNAIII-specific radiolabeled DNA. Membrane was autoradiographed and density of bands determined.

To test if rRAP is active and can induce RNAIII synthesis, *S. aureus* cells containing rnaiii::blaZ fusion construct were incubated with increasing amounts of rRAP. As controls, cells were incubated only with growth medium (negative control). RNAIII (as β-lactamase activity) was detected by the addition of nitrocefin, a yellow substrate that turns pink in the presence of β-lactamase. This method is useful when the difference between experimental and control groups is at least twice, and one group turns pink while the other remains yellow. As shown in FIG. 3A, rRAP activates RNAIII synthesis in a concentration dependent manner, reaching threshold levels at 2.25 nmole/$10^7$ bacteria. Activation of RNAIII by recombinant RAP was similar to that of partially purified RAP. The increase in RNAIII synthesis (β-lactamase activity) in the presence of 2.25 nmole rRAP is significant ($P<0.00169$) as compared to no addition of rRAP. We also tested induction of RNAIII synthesis by Northern blotting, where cells were grown for 30 min with or without rRAP, cells collected, Northern blotted, and the presence of RNAIII was detected using RNAIII-specific radiolabeled DNA. Membrane was autoradiographed and density of bands determined. As shown in FIG. 3B, rRAP induced the synthesis of RNAIII.

TRAP

Trap is Necessary for *S. aureus* Pathogenesis

Figure 6A:
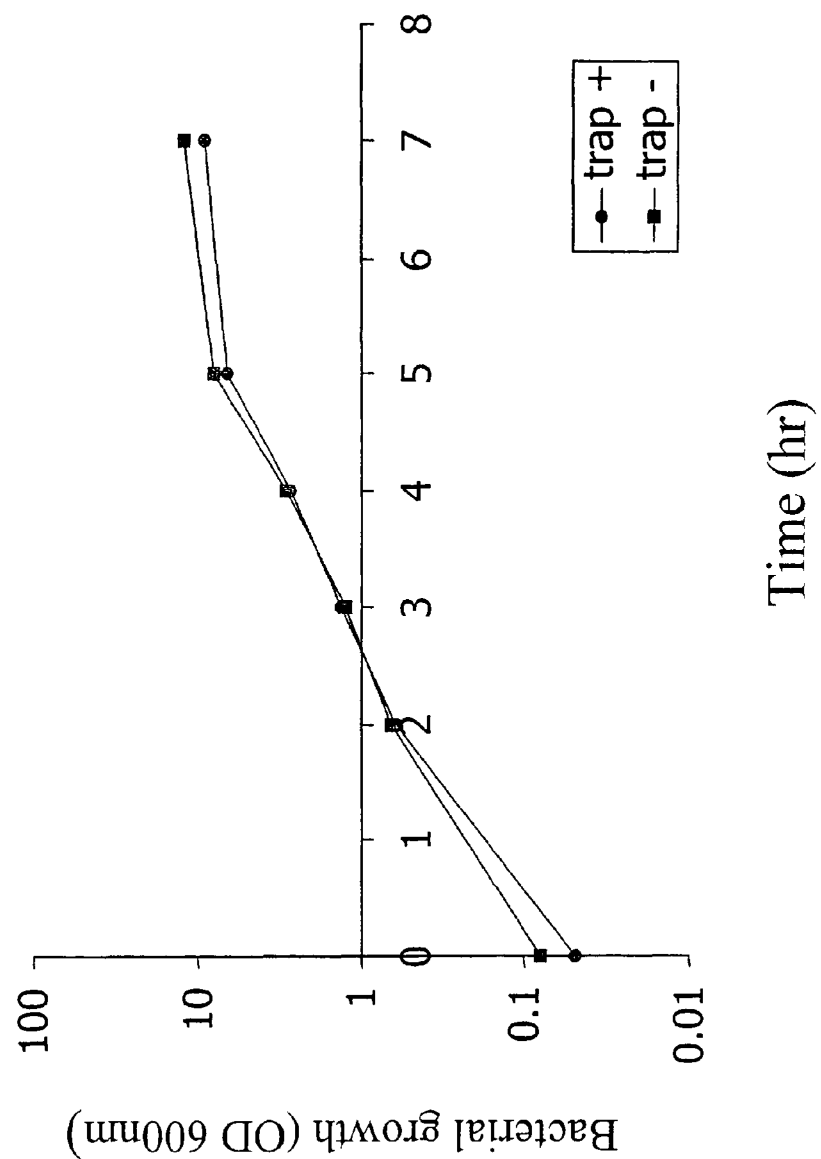
FIG. 6A is a growth curve for cells grown from the early exponential phase for several hrs and their density determined (OD 600 nm) at time intervals. Circle: TRAP+. Square: TRAP$^-$.
Figure 6B:
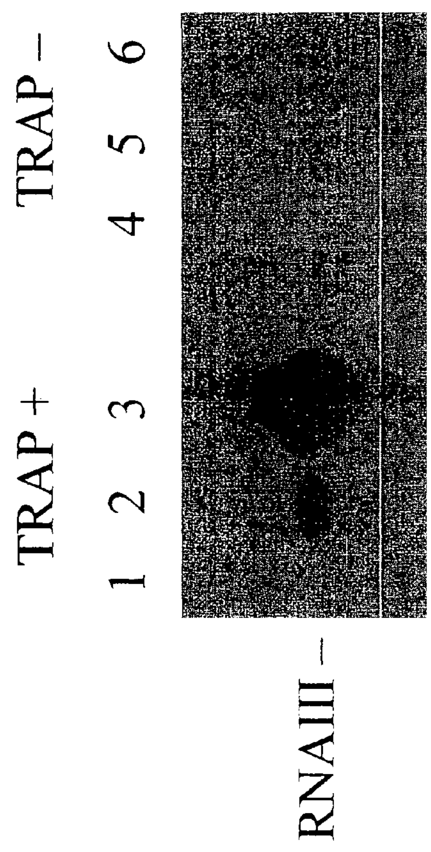
FIG. 6B is a photograph of a gel showing cell samples from each growth phase (equivalent to ~$3\times10^8$ cells) reflected in FIG. 6A. Cells were collected, Northern blotted, and the presence of RNAIII was detected using RNAIII-specific radiolabeled DNA. The membrane was autoradiographed. *S. aureus* TRAP+ (lanes 1, 2, 3) and *S. aureus* TRAP (lanes 4, 5, 6). Lanes 1, 4: Early exponential. Lanes 2, 5: mid-exponential. Lanes 3, 6: post-exponential.

RAP has been shown to induce and RIP has been shown to inhibit TRAP phosphorylation [5]. To show that TRAP is important for *S. aureus* pathogenesis, the traP gene was disrupted in *S. aureus* 8325-4 and the parent strain (TRAP+) and the mutant strain ($TRAP^-$) were tested for growth, RNAIII synthesis, toxin production and pathogenesis. To test for cell growth and RNAIII synthesis, cells were grown from the early to the post-exponential phase of growth. At time intervals cell density was determined and cell samples from each growth phase were collected, Northern blotted, and the presence of RNAIII was detected using RNAIII-specific radiolabeled DNA. As shown in FIG. 6A, no difference in cell growth was observed between TRAP+ and TRAP⁻ strains. The synthesis of RNAIII in the TRAP+ strain was observed from the mid-exponential phase but was absent in the TRAP⁻ strain (FIG. 6B), confirming that TRAP is an important factor in the induction of RNAIII synthesis.

Figure 7A:
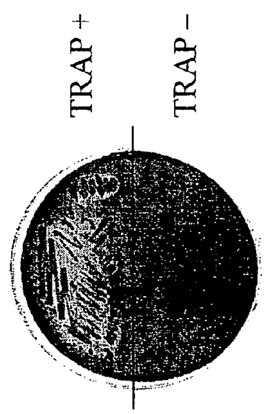
FIG. 7A is a photograph that shows cells grown on a sheep blood agar plate to test for hemolysis. Hemolysis by TRAP+is represented on the portion of the figure and TRAP$^-$ is represented on the bottom.

RNAIII is known to upregulate the production of many of the toxins produced by *S. aureus*, some of which are hemolysins [2]. To test for the production of hemolysins, the TRAP+ and TRAP⁻ strains were grown on a sheep blood agar plate overnight at 37° C. and then at 4° C. (to test for both α and β hemolysins). As shown in FIG. 7A, no hemolysis was observed in the TRAP⁻ strain, confirming that TRAP is an important factor in toxin production.

Figure 7B:
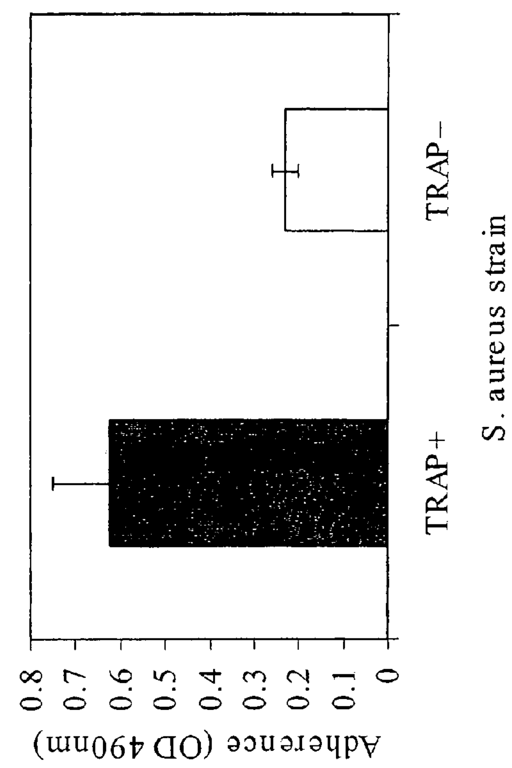
FIG. 7B is a graph depicting adherence of early exponential *S. aureus* TRAP+ and TRAP$^-$ strains that were grown at 37° C. for 4 hrs in polystyrene microtiter plates. Adherent bacteria were stained with safranin and absorbance determined at 490 nm.

To test whether TRAP is important for biofilm formation, the TRAP+ and TRAP⁻ strains were grown in polystyrene wells and adherent bacteria was stained by safranin. As shown in FIG. 7B, safranin staining was greatly reduced in the TRAP strain, suggesting that TRAP is an important factor in cell adhesion and biofilm formation.

Figure 8:
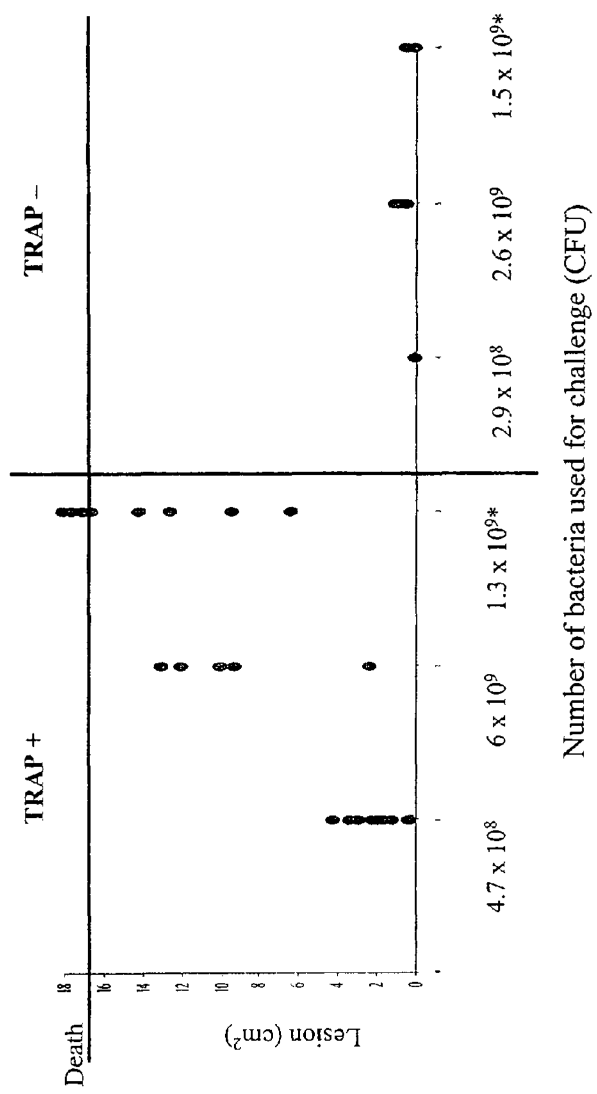
FIG. 8 is a graph depicting lesion size vs. *S. aureus* 8325-4 parent strain (TRAP+) (left panel) and the *S. aureus* 8325-4 (TRAP$^-$) mutant strain (right panel).

To test the importance of TRAP in S. aureus pathogenesis in vivo, the TRAP+ and TRAP⁻ strains were injected subcutaneously into mice and animals were followed for mortality, the development of lesion and overall health. As shown in FIG. 8, all animals (n=10) that were injected with $4\times10^8$ CFU (of TRAP+ that were grown on a plate) developed a lesion with an average size of 1.74 $cm^2$. All animals (n=5) that were injected with $6\times10^9$ CFU (of TRAP+ that were grown on a plate) developed a lesion with an average size of 9.4 $cm^2$. Of 8 animals (n=8) that were injected with $1.3\times10^9$ CFU (TRAP+ that were grown in culture (*)), 4 died within the first 24 hrs and the rest developed a large lesion, with an average size of 8.63 $cm^2$. On the other hand, all animals that were injected with the TRAP⁻ strain seemed perfectly healthy, including the few that developed a very small lesion. Specifically, none of the animals (n=10) that were injected with $3\times10^8$ CFU of TRAP⁻ that were grown on a plate developed a lesion. All animals (n=5) that were injected with $2.6\times10^9$ CFU of TRAP⁻ that were grown on a plate developed a small lesion with an average size of 0.62 $cm^2$ Of the animals (n=8) that were injected with $1.5\times10^9$ CFU of TRAP⁻ that were grown in culture (*), 7 animals developed no lesion at all and one animal developed a small lesion of 0.4 $cm^2$ (average size of 0.05 cm 2). The differences in lesion size between the animals that were injected with the TRAP+ or TRAP⁻ strains is significant ($p<0.0008$). These results confirm that the expression of TRAP is important for *S. aureus* pathogenesis and opens the field further for the development of novel drugs to prevent or treat staphylococcal infections.

Amino Acid Sequence Analysis of TRAP

The traP gene in various clinical isolates of *S. aureus* and *S. epidermidis* was amplified by PCR, and its sequence determined. Comparison of these sequences to BLAST searches in different databases (including the NCBI Microbial Genomes Databases, such as ncbi.nlm.nih.gov/Microb_blast/unfinishedgenome.html) indicates that TRAP is unique to *staphylococci*. Comparison of the deduced amino acid sequences of the *S. aureus* and *S. epidermidis* TRAP proteins shows that they are highly conserved among *staphylococci*. Multi sequence alignment analysis (Clustal W) of *S. aureus* TRAP protein sequences from the various strains indicates that its sequence is divided into two sub-groups (FIG. 9). Group I includes TRAP in 8325, which is identical to TRAP in COL, MSSA476, Mu50/ATCC700699 and N315 (16) and our clinical nare-isolates #7 and 11. Group II includes TRAP in our clinical nare-isolates 12 and 15 and MRSA252 (Sanger Centre Database). TRAP of Group I is ~97% identical to that of Group II (an E-value determined with the BLASTP algorithm is $2\times10^{-84}$). Similarity of both group I TRAP and Group II TRAP sequences to that of *S. epidermidis* is approximately 86% (an E-value is $9\times10^{-65}$).

*S. aureus* clinical isolate #12 has an insertion of IS1181 exactly in front of the TRAP stop codon (GenBank accession number AJ489447). Insertion of IS1181 shifted the native traP stop codon but introduced another stop codon 27 bp downstream that elongated TRAP from 167 to 176 AA (TRAP+GSSSFMVGR) (SEQ ID NO: 16) (FIG. 9). Like other clinical or lab strains, TRAP is phosphorylated and RNAIII is expressed in strain isolate #12, suggesting that the insertion element does not disrupt its function (not shown).

Secondary Structure Predictions of TRAP

Figure 10:
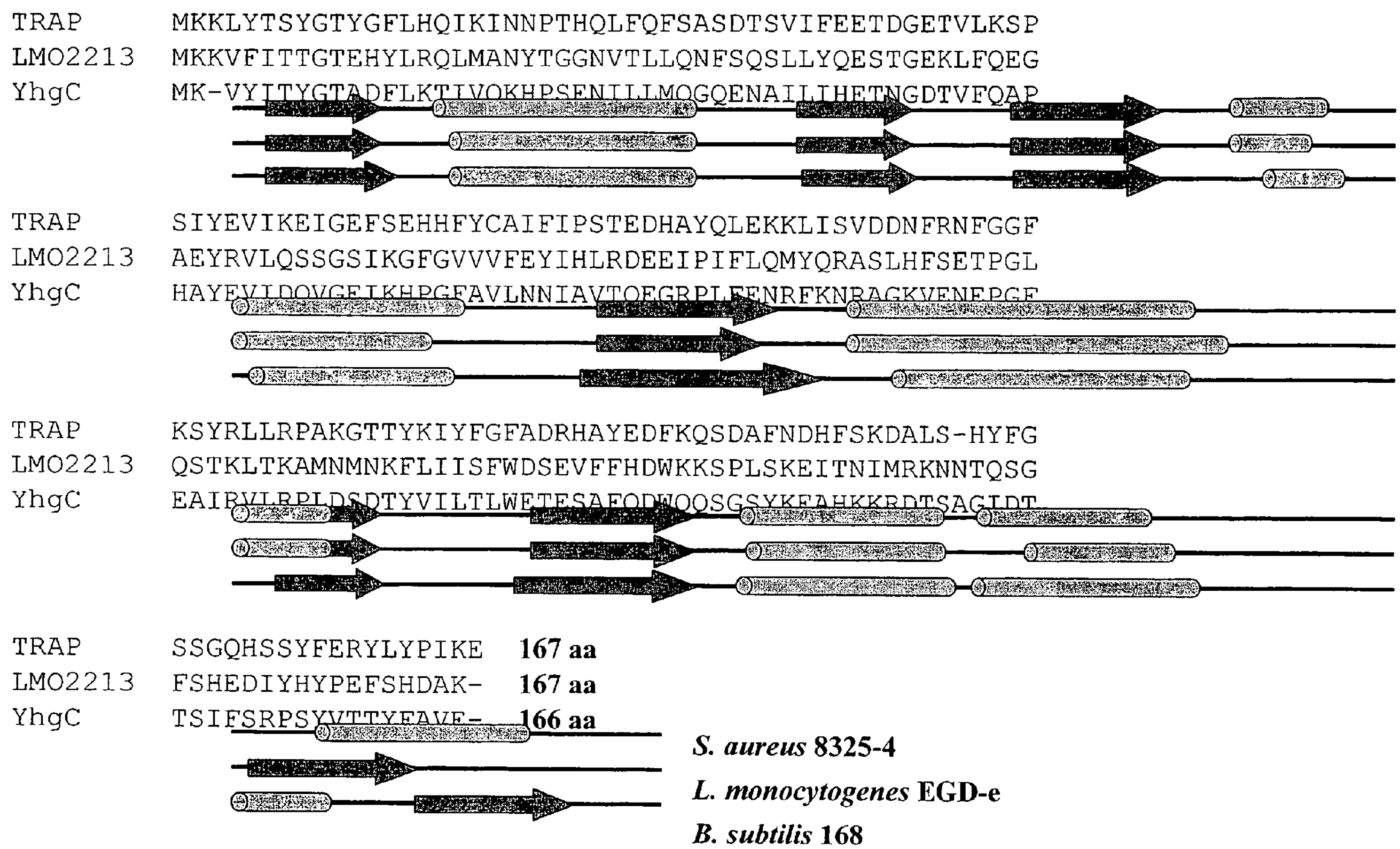
FIG. 10 shows secondary structures predictions of TRAP and its homologues. Alignment of deduced amino acid sequences of *S. aureus* TRAP (GenBank AF202641) (SEQ ID NO: 18), *L. monocytogenes* LM02213 (GenBank AL591982) (SEQ ID NO: 19) and *B. subtilis* yhgc (GenBank Z99109) (SEQ ID NO: 20) supplemented with their putative secondary structures predicted by use of the PSIPRED (2.4) coils are shown as solid lines, helices as horizontal cylinders and strands as arrows.

TRAP is highly unique to Staphylococci, but has some sequence similarity to the hypothetical protein yhgC protein in *Bacillus subtilis* (GenBank Accession Number Z99109) (an E-value is $9\times10^{-15}$). Interestingly, in addition to Bacillus subtilis, among more than 160 eubacterial genomes, only in *Bacillus anthracis*, which is 97% identical to that of *B. cereus* (TIGR database), *Listeria innocua* and *L. monocytogenes* ORFs could be identified which have some sequence similarity to TRAP (E-values are 0.005, 0.035 and 0.1, respectively). Like TRAP, all ORFs are of exactly 167 AA except for yhgC, which is 166 AA (FIG. 10).

The secondary structure of these proteins was predicted using the protein structure prediction server The PCIPRED v.2.4 [bioinf.cs.ucl.ac.uk/psiform.html/]. Interestingly, although the sequence similarity of these ORFs is very low, their predicted secondary structures are very similar to that of TRAP (FIG. 10).

Figure 11:
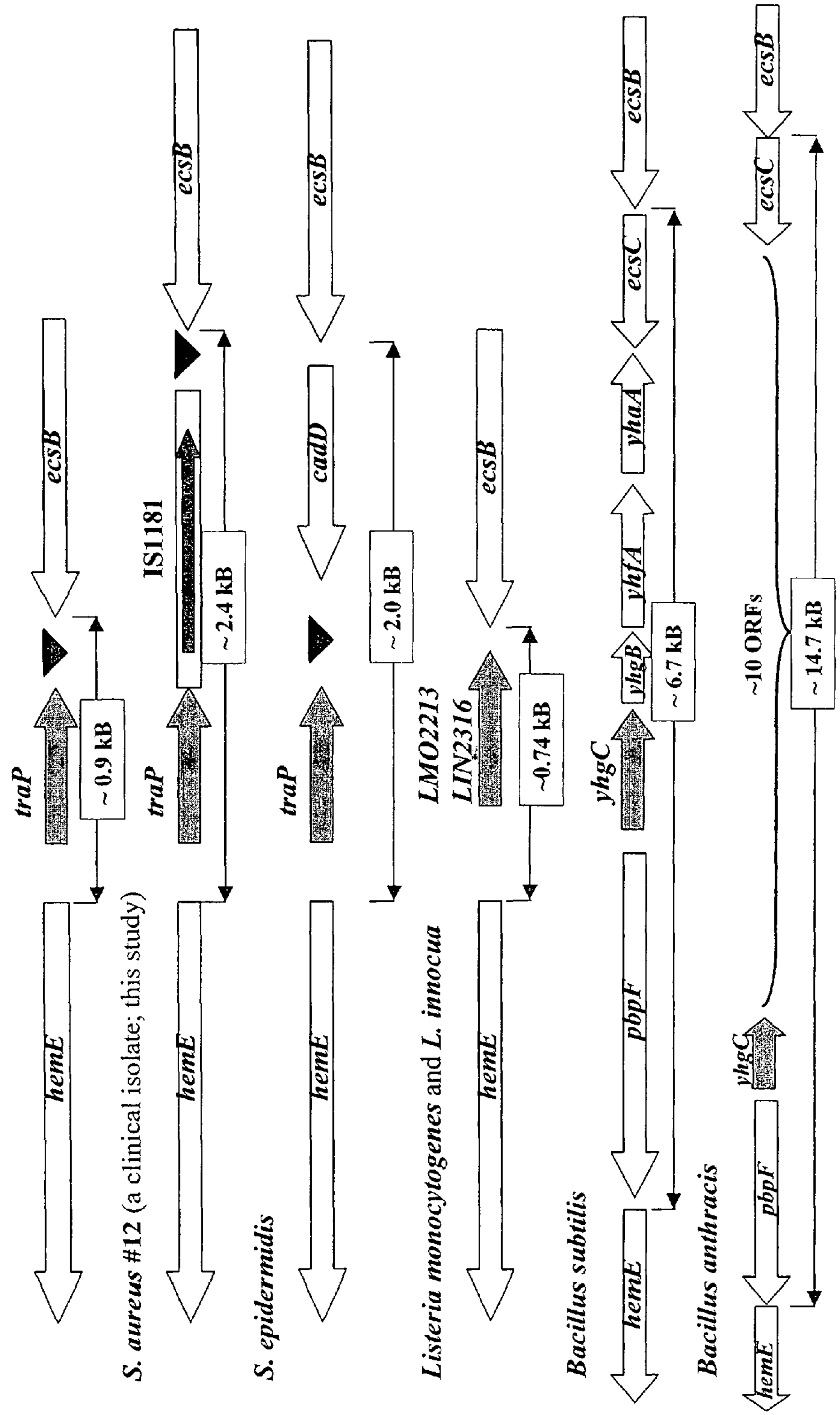
FIG. 11 shows gene region maps that were designed on the basis of DNA sequences obtained from GenBank and corresponding genome project databases. The *S. aureus* traP (AF202641 and this study) and its homologues in *S. epidermidis* (TIGR database and this study), *Listeria monocytogenes* (AL591982), *L. innocua* (AL596171), *Bacillus subtilis* (Z99109) and *B. anthracis* (TIGR database) are shown as gray arrows; inverted black triangles indicate a putative transcriptional terminator. A distance (in kB) between flanking hemE and ecsB genes is shown within an interrupted two-head arrow. hemE gene encodes an enzyme of the late step of the protoheme IX biosynthetic pathway, ecsBC genes encode components of the protein secretion apparatus as well as secretory protein genes transcription in a coordinated fashion (*B. subtilis*); cadD gene is strongly similar to that of the *S. aureus* plasmid pRW001; pbpF gene codes for a penicillin-binding protein involved in the *B. subtilis* germination process; genes yhgB, yhfA and yhaA encode hypothetical proteins of unknown functions.

Chromosomal Organization of the *S. aureus* TRAP Gene Region and Comparison with Other Gram-positive Eubacteria The same organization of the TRAP gene region is found in all *Staphylococcus* spp. (in both *S. aureus* and *S. epidermidis*) genomes (FIG. 11). The TRAP gene is flanked by two polycistronic operons; one of them (upstream of traP) encodes enzymes of the late step of the protoheme IX biosynthetic pathway (hemEHYgenes), the second (downstream of traP) codes for a putative multi protein transporting system (ecsAB (C) genes). The direction of the traP gene transcription is opposite to both hem and ecs operons. The same organization is found also in yhgC region in *B. subtilis, B. anthracis* and in the TRAP-like ORFs in *Listeria* (FIG. 11). These results suggest that TRAP represents a class of signal transducers in bacteria and that it can be a target site for therapy in many bacterial species in addition to *Staphylococci.*

Figure 12:
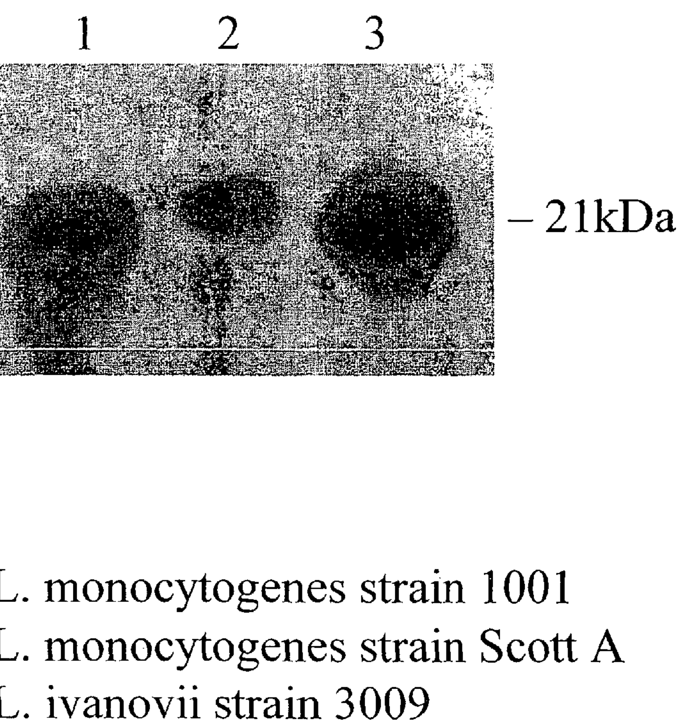
FIG. 12 is a photograph of a gel showing in vivo phosphorylation of *Listeria monocytogenes* strain 1001 (lane 1), L monocytogenes strain ScottA (lane 2, and *L. ivanovii* strain 3009, by growing early exponential cells with $p^{32}$ for 1 hr Total cell homogenate was separated by SDS PAGE and the gel autoradiographed.

Phosphorylation of TRAP and TRAP Like Molecules and Inhibition of TRAP Phosphorylation by RIP Because TRAP-like molecules are found in other bacterial species in addition to *Staphylococci*, we tested whether they can undergo phosphorylation. We grew various strains of *Listeria* (*L. monocytogenes* and *L. ivanovii*) and various strains of *Bacillus anthracis, B. subtilis* and *B. cereus*) with $p^{32}$, and tested for phosphorylation of TRAP (21 kDa) by SDS PAGE followed by autoradiography. As shown in FIG. 12 for *Listeria* spp, a 21 kDa protein was in vivo phosphorylated, as expected. Similar results were obtained for *Bacillus* spp. (not shown). These results suggest that pathogenesis may also be regulated via TRAP phosphorylation in bacteria expression TRAP-like proteins.

Figure 13:
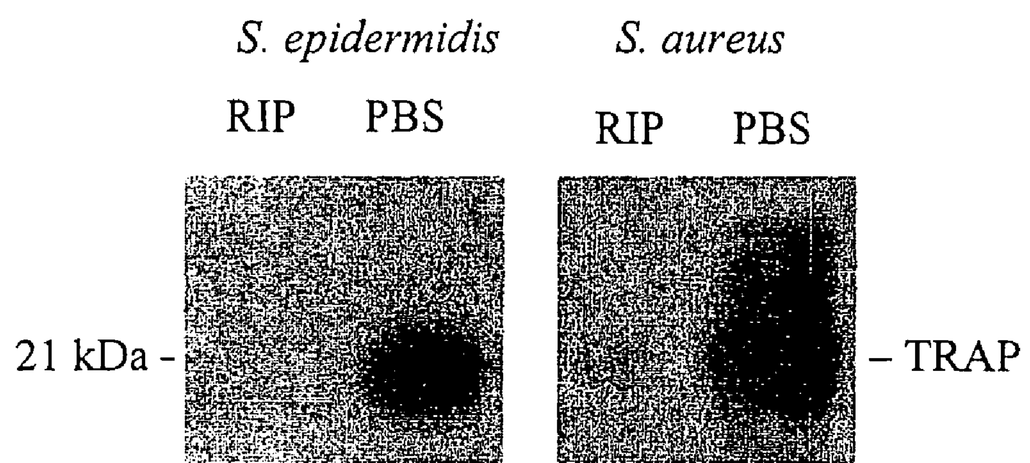
FIG. 13 is a photograph of a gel showing that RIP inhibits TRAP phosphorylation both in *S. aureus* and in *S. epidermidis*. *S. aureus* (right panel) and *S. epidermidis* (left panel) were in vivo phosphorylated for 1 hr in the presence or absence of RIP. Total cell homogenate was separated by SDS PAGE and the gel was autoradiographed.

To test for TRAP phosphorylation in *S. epidermidis*, in vivo phosphorylation assays were carried out as described for *S. aureus [*5]. Briefly, early exponential *S. epidermidis* were grown in the presence of phosphate-free buffer supplemented with radiolabeled orthophosphate with or without RIP (10 $\mu g/10^7$ cells). After a 1 hr incubation period, the cells were collected by centrifugation, treated with lysostaphin followed by the addition of sample buffer, and total cell homogenate was applied without boiling to 15% SDS PAGE and the gel autoradiographed. The same experiment was carried out on 6390B *S. aureus* cells as a positive control. Results (FIG. 13) show that TRAP phosphorylation can be inhibited by RIP also in *S. epidermidis*. These results are not surprising in view of the fact that TRAP is found also *S. epidermidis*, and they show that TRAP phosphorylation and expression is important for staphylococcal pathogenesis. Because its sequence is highly conserved among staphylococcal strains and species and because its secondary structure is similar to many TRAP-like molecules in other bacteria, TRAP can be a target site for therapy in many bacterial species in addition to *Staphylococci.*

RIP

Figure 14A:
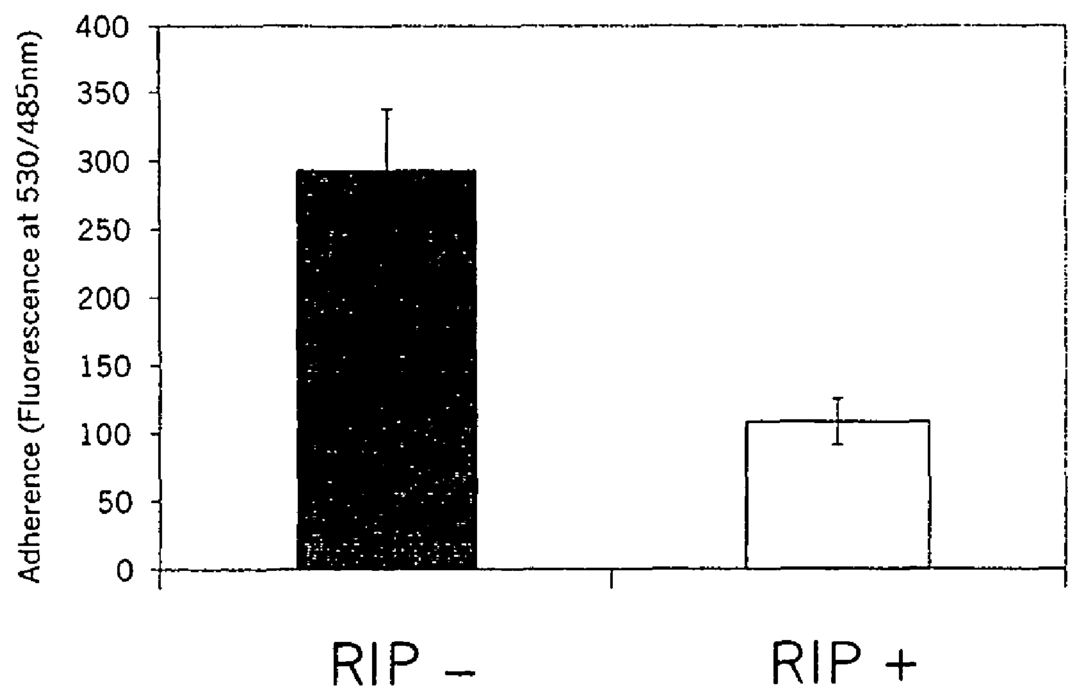
FIG. 14A is a graph depicting adherence in the presence of RIP (RIP+) and in the absence of RIP (RIP−). FITC-labeled bacterial cells ($10^6$ CFU) were applied to microtiter plates containing confluent $10^4$ HaCat cells, in the presence or absence of 5 μg RIP (RIP+/−). Cells were incubated for 30 min at 37° C., washed in PBS and fluorescence at 485/530 nm was determined.

RIP (native or synthetic, YSPWTNF (SEQ ID NO: 26) or derivatives) has been shown not only to inhibit RNAII and RNAIII synthesis and thus to inhibit toxin production [13, 18] but has also been shown to inhibit *S. aureus* adherence to human cells and to inhibit the formation of biofilm on plastic [16]. Virulence of *S. epidermidis* is also often associated with their ability to adhere to host cells and to form biofilm on medical devices. To test whether RIP can prevent *S. epidermidis* from colonizing host cells and therefore be a candidate for therapy and prevention, FITC-labeled *S. epidermidis* were incubated in the presence or absence of RIP with a confluent layer of keratinocytes (HaCat cells) for 30 min. As shown in FIG. 14A, RIP significantly ($p<0.05$) reduced *S. epidermidis* adherence to HaCat cells.

Figure 14B:
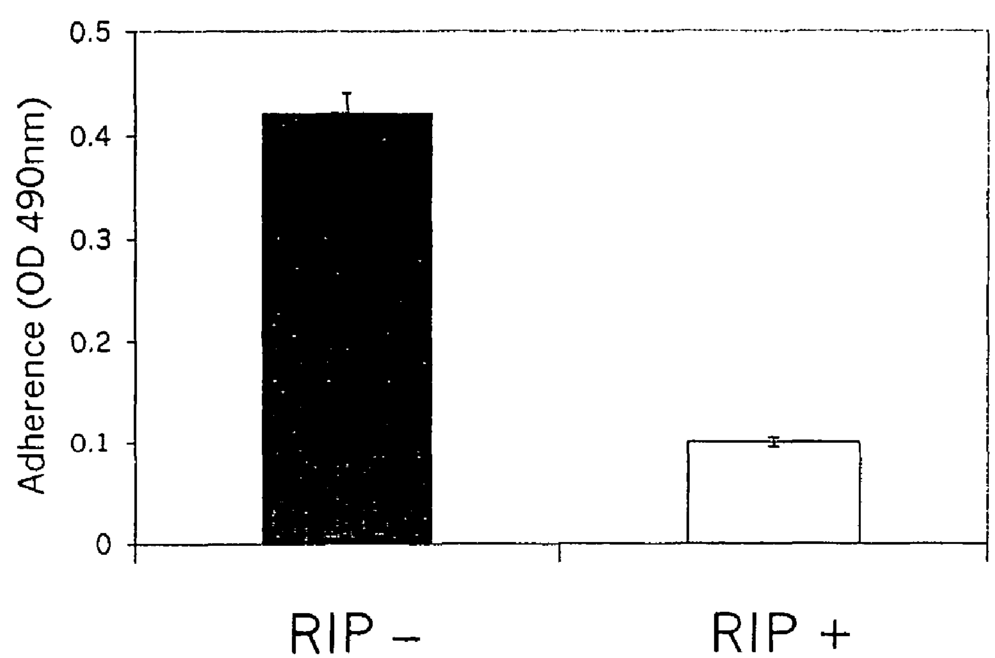
FIG. 14B is a graph depicting adherence in the presence of RIP RIP+ and in the absence of RIP RIP−. *S. epidermidis* were grown in polystyrene plates for 3 hrs, adherent bacteria were stained by safranin, and absorbance at 490 nm was determined.
Figure 17:
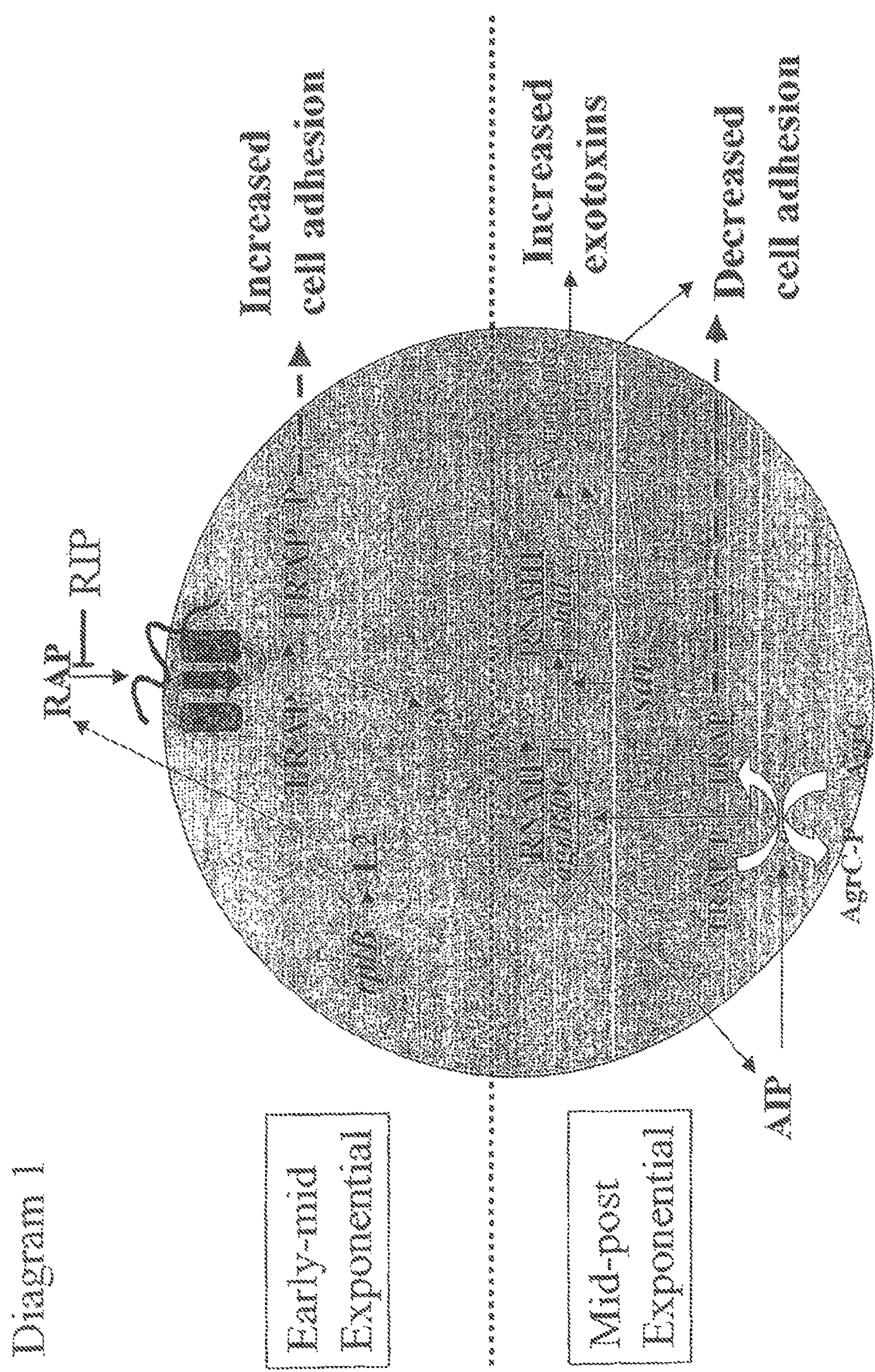
FIG. 17 is a diagram identified as Diagram 1. Proposed mechanism of *S. aureus* pathogenesis.

To test whether RIP reduces adherence and biofilm formation of *S. epidermidis* to plastic, early exponential *S. epidermidis* were grown for 3 hrs in microtiter plates made of polystyrene, and adherent cells were stained with safranin. These experimental conditions allow for biofilm to be formed (as observed by atomic force microscopy, not shown). As shown in FIG. 14B, RIP significantly reduced the number of cells that adhered to the plastic. These results clearly demonstrate that RIP inhibits the adhesion of *S. epidermidis* to host cells and to plastic in vitro.

RIP can Protect from a Graft-associated Infections and is Synergistic to Antibiotics To test if RIP can prevent graft-associated infections, rat-graft model was used.

Methods

Induction of Graft-associated Infection

Rats (Wistar adult males (300-350 g), n=15/experimental group) were anaesthetized, hair on their back shaved and the skin cleansed with 10% povidone-iodine solution. A subcutaneous pocket was made on the side of the median line by a 1.5 cm incision. Aseptically, 1 $cm^2$ sterile collagen-sealed Dacron graft (Albograft™, Sorin Biomedica Cardio, S.p.A., Saluggi VC, Italy) was implanted into the pocket. Immediately prior to implantation, the Dacron grafts were soaked for 20 min in sterile solutions of 10 mg/l RIP in saline or saline only or inactive RIP peptide analogue (YKPETNF) (SEQ ID NO: 32) as controls, with or without antibiotics (mupirocin 100 mg/l, quinupristin-dalfopristin 50 mg/l, levofloxacin 30 mg/l, rifampin 5 mg/l). Pockets were closed by skin clips and 1 ml sterile saline solution with or without $2\times10^7$ bacteria was inoculated onto the graft surface using a tuberculin syringe to create a subcutaneous fluid-filled pocket. Some of the animals that had grafts soaked only with RIP or saline were injected intraperitoneally with antibiotics (cefazolin 30 mg/kg, imipenem 30 mg/kg, teicoplanin 10 mg/kg, levofloxacin 10 mg/kg). Grafts were explanted 7 days following implantation. Estimated RIP that adhered to graft was 10-26 μg.

Assessment of Graft Infection

The explanted grafts were placed in sterile tubes, washed in sterile saline solution, placed in tubes containing 10 ml of phosphate-buffered saline solution and sonicated for 5 min to remove the adherent bacteria from the grafts. Quantitation of viable bacteria was performed by culturing serial 10-fold dilutions (0.1 ml) of the bacterial suspension on blood agar plates. All plates were incubated at 37° C. for 48 hr and evaluated for the presence of the strain. Bacteria were quantitated by counting the number of colony forming unites (CFU) per plate. To determine if bacteria were efficiently removed from the graft, washed and sonicated grafts were observed under a Nikon Eclipse E 600 optical microscope (Nikon Y-THS, Japan).

Statistical Analysis

Quantitative culture results of the in vivo experiments were presented as mean+SD of the mean. Comparisons of the results were performed by the analysis of variance (ANOVA) on the log-transformed data. Statistical analysis was performed for in vitro adhesion assays using Student's t-Test by Microsoft Excel (Microsoft, Wash.). Significance was accepted when the P value was $<0.05$.

Results

To test if RIP can prevent graft-associated infections, Dacron grafts were coated with or without RIP, and with or without various types of antibiotics (for local prophylaxis experiments). Coated grafts were implanted in rats, bacteria injected into the implants, implants removed after a week, and bacterial load determined. Alternatively, Dacron grafts were first coated with RIP, bacteria injected, and antibiotics were administered by the intraperitoneal route (for parenteral prophylaxis experiments). As a negative control, grafts were implanted without local or parenteral RIP/antibiotics prophylaxis and no bacteria were injected. As a positive control, grafts were implanted, bacteria were injected, but no RIP/antibiotics prophylaxis was given. As a negative control to RIP, an inactive form of RIP analogue (YKPETNF) (SEQ ID NO: 32) was used instead of RIP.

The results (Table 2) clearly indicate that RIP reduces bacterial load of all strains tested by log 3, and that when it is applied together with some antibiotics, it can eliminate bacterial load by 100%. Specifically, 1) None of the animals included in the uncontaminated negative control group had microbiological evidence of graft infection.

2) All 15 rats included in the contaminated untreated positive control group demonstrated evidence of graft infection, with quantitative culture results showing $6.8\times10^6$<≡~$1.9\times10^6$ CFU/ml, $8.1\times10^6\pm2.2\times10^6$ CFU/ml, $7.3\times10^6$35 $6.4\times10^5$ CFU/ml for the inoculated GISE strain, MRSE strain and MSSE strain, respectively. Grafts coated with the inactive RIP peptide analogue demonstrated evidence of graft infection similarly to untreated controls, with quantitative culture results showing $6.52\times10^6\pm3\times10^6$ CFU/ml, $7.08\times10^6\pm2.1\times10^6$ CFU/ml, $5.4\times10^6\pm8\times10^5$ CFU/ml for the inoculated GISE strain, MRSE strain and MSSE strain, respectively.

3) All groups with 10 mg/l RIP-soaked Dacron grafts showed evidence of decreased intensity of staphylococcal infection compared to the untreated control group, with. $6.2\times10^4\pm2.0\times10^4$CFU/mL ($p<0.05$), $7.4\times10^3\pm1.8\times10^3$ CFU/mL ($p<0.0001$), $9.1\times10^3\pm2.3\times10^3$ CFU/mL ($p<0.001$), for inoculated GISE strain, MRSE strain and MSSE strain, respectively.

4) In the rats inoculated with GISE, RIP graft treatment was inhibiting bacteria better than the parenteral antibiotics prophylaxis (>10 to 100 fold), (see Table 2B) and was still more effective than levofloxacin and rifampicin local prophylaxis, but not as effective as mupirocin and quinopristin-dalfopristin local prophylaxis (see Table 2A).

In the rats inoculated with MRSE or MSSE, RIP treatment was equally or more effective than most antibiotics, with the exception of teicoplanin in the parenteral prophylaxis experiments (see Table 2B) and mupirocin, quinupristin-dalfopristin in the local prophylaxis (see Table 2A).

5) When RIP graft treatment was associated with antibiotic prophylaxis, the level of inhibition of bacterial load was greater (if compared to the single agents alone), and in some cases it reached 100%, as in the case of RIP with teicoplanin given parenterally for the MRSE and MSSE strains ($p<0.001$ vs. single agents) (see Table 2B), and in the case of RIP with mupirocin or with quinupristin-dalfopristin given locally, for all strains ($p<0.001$ vs. single agents) (see Table 2B).

Similar results were obtained with *S. aureus* MRSA, MSSA and GISA and with vancomycin-resistant *S. aureus* and *S. epidermidis* strains VISA and VISE (not shown).

RIP can Protect from Graft Associated Infections In Vivo

Animals (15/group) received a Dacron-graft implanted in a subcutaneous pocket. Graft was subsequently infected with either *S. epidermidis* (tested on MSSE, MRSE and GISE) or with *S. aureus* (tested on MSSA, MRSA and GISA). The Dacron-graft prior to implantation was soaked in saline with or without 20 mg/l of RIP and some animals received 10 mg/l of RIP i.p. as a prophylaxis treatment. Results are summarized in Tables 3A and 3B).

These results clearly show that RIP can be used to coat medical devices to prevent any type of staphylococcal infections and that RIP is synergistic to antibiotics.

TABLE 2

Prevention of *S. epidermidis* infection using RIP-coated Dacron grafts in the presence or absence of local (A) or parenteral (B) antibiotic prophylaxis.

| Treatment | GISE $\times 10^4$ CFU/ml ± SD | MRSE $\times 10^4$ CFU/ml ± SD | MSSE $\times 10^4$ CFU/ml ± SD |
|---|---|---|---|
| A. Local prophylaxis Bacterial concentration is $\times 10^4$ CFU/ml ± SD | | | |
| Control (untreated) | 680 ± 190 | 810 ± 220 | 730 ± 64 |
| RIP | 6.2 ± 2.4 | 0.74 ± 0.18 | 0.91 ± 0.23 |
| Levofloxacin | 280 ± 40 | 6.8 ± 2.5 | 4.2 ± 2.1 |
| Levofloxacin + RIP | 4.9 ± 0.79 | 0.26 ± 0.057 | 0.58 ± 0.072 |
| Mupirocin | 0.07 ± 0.018 | 0.035 ± 0.014 | 0.064 ± 0.015 |
| Mupirocin + RIP | 0.000 ± 0 | 0.000 ± 0 | 0.000 ± 0 |
| Rifampicin (Refampin) | 84 ± 27 | 0.8 ± 0.37 | 0.73 ± 0.2 |
| Rifampicin + RIP | 5.9 ± 2.2 | 0.064 ± 0.013 | 0.031 ± 0.01 |
| Quinupristin-Dalfopristin (Q/D) | 0.0069 ± 0.0013 | 0.0048 ± 0.001 | 0.0026 ± 0.0003 |
| Quinupristin-Dalfopristin + RIP | 0.000 ± 0 | 0.000 ± 0 | 0.000 ± 0 |
| B. Parenteral prophylaxis Bacterial concentration is $\times 10^4$ CFU/ml ± SD | | | |
| Control (untreated) | 680 ± 190 | 810 ± 220 | 730 ± 64 |
| RIP | 6.2 ± 2 | 0.74 ± 0.18 | 0.91 ± 0.23 |
| Cefazolin | 590 ± 200 | 370 ± 120 | 0.64 ± 0.19 |
| Cefazolin + RIP | 4.2 ± 1.6 | 0.35 ± 0.11 | 0.058 ± 0.034 |
| Teicoplanin | 57 ± 24 | 0.072 ± 0.008 | 0.0084 ± 0.0004 |
| Teicoplanin + RIP | 2.4 ± 1.8 | 0.000 ± 0 | 0.000 ± 0 |
| Imipenem | 89 ± 36 | 4 ± 1.8 | 0.73 ± 0.2 |
| Imipenem + RIP | 4 ± 2.5 | 0.088 ± 0.017 | 0.043 ± 0.012 |
| Levofloxacin | 480 ± 170 | 3.9 ± 1.4 | 3.5 ± 1.1 |
| Levofloxacin + RIP | 3.9 ± 3.3 | 0.29 ± 0.037 | 0.29 ± 0.055 |

TABLE 3

RIP prevents Dacron-graft associate *S. epidermidis* (A) and *S. aureus* (B) infections.

| Treatment | GISE $\times 10^4$ CFU/ml ± SD | MRSE $\times 10^4$ CFU/ml ± SD | MSSE $\times 10^4$ CFU/ml ± SD |
|---|---|---|---|
| A | | | |
| Control (untreated) | 880 ± 240 | 680 ± 110 | 710 ± 150 |
| RIP local | 0.46 ± 0.13 | 0.087 ± 0.023 | 0.08 ± 0.024 |
| RIP parenteral | 0.31 ± 0.6 | 0.052 ± 0.017 | 0.067 ± 0.019 |
| RIP local + RIP parenteral | 0.00 ± 0 | 0.00 ± 0 | 0.00 ± 0 |
| B | | | |
| Control (untreated) | 4000 ± 1700 | 3000 ± 300 | 4900 ± 2100 |
| RIP local | 0.70 ± 0.28 | 0.62 ± 0.21 | 0.55 ± 0.19 |
| RIP parenteral | 0.49 ± 0.11 | 0.29 ± 0.088 | 0.045 ± 0.009 |
| RIP local + RIP parenteral | 0.00 ± 0 | 0.00 ± 0 | 0.00 ± 0 |

Identifying a Gents Suitable for Preventing and/or Treating Staphylococcal Infections Of particular interest in the present invention is the identification of agents that have activity in affecting the expression and/or function of RAP and/or TRAP. In general agents of interest are those that inhibit RAP or TRAP activity, e.g., by inhibiting the ability of RAP to effect activation of RNAIII synthesis. Such agents are candidates for development of treatments for infection of pathogenic *Staphylococcus*. Of particular interest are screening assays for agents that have a low toxicity for human cells and/or high specificity for *Staphylococcus*, preferably with substantially no or little pressure for selection of strains resistant to the action of the agent, and without substantially affecting normal flora of the host (e.g., as distinguished from wide-spectrum antibiotics).

The term "agent" as used herein describes any molecule, e.g., protein or pharmaceutical, with the capability of altering RAP or TRAP activity, or mimicking or enhancing RIP activity, as described above. Generally a plurality of assay mixtures are run in parallel with different agent concentrations to detect differential responses to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, pheromones, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial (e.g., non-pathogenic *Staphylococcus*), fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs, and can contain protective groups e.g., prolyl, or can contain D-amino acids.

Screening of Candidate Agents

A wide variety of in vitro assays may be used to screen candidate agents, including labeled in vitro binding assays, e.g., protein-protein binding, protein-DNA binding assays, electrophoretic mobility shaft assays, immunoassays for protein binding, and the like. Purified naturally-occurring or recombinant or synthetic RAP, TRAP and/or RIP polypeptides, and/or synthetically produced peptides or fragments of RAP TRAP and/or RIP, can be used in various screening assays to identify ligands or substrates that bind to, modulate (e.g., increase or inhibit), or mimic the action of the native proteins. The purified proteins may also be used for determination of three-dimensional crystal structure, which can be used for modeling intermolecular interactions, transcriptional regulation, etc.

The screening assay can be a binding assay, wherein one or more of the molecules may be joined to a label, and the label directly or indirectly provides a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures. In general, the particular type of screening assay employed will preferably be one amenable to parallel, simultaneous screening of a large number of candidate agents.

Screening assays of the present invention encompass assays that examine the effect of candidate agents on the roles of RAP, TRAP and RIP in RNAIII production and/or virulence factor production. For example, the candidate agent may be contacted with pathogenic *Staphylococcus* and the levels of rnaiii transcription in the presence of the agent compared to rnaiii transcription levels in the presence of RIP, RAP, TRAP and/or a combination of RIP, RAP and TRAP. Such screening assays can utilize recombinant host cells containing reporter gene systems such as CAT (chloramphenicol acetyltransferase), β-galactosidase, and the like operably associated with maiii or virulence factor genes to facilitate detection of rnaiii or virulence gene transcription or to facilitate detection of RNAIII or virulence factor production. Alternatively, the screening assay can detect rnaiii or virulence factor transcription using hybridization techniques (e.g., Northern blot, PCR, etc.) well known in the art.

A variety of other reagents may be included in the screening assays described herein. Where the assay is a binding assay, these include reagents like salts, neutral proteins, e.g. albumin, detergents, etc., that are used to facilitate optimal protein-protein binding, protein-DNA binding, and/or reduce non-specific or background interactions. Reagents that improve the efficiency of the assay, such as protease inhibitors, nuclease inhibitors, antimicrobial agents, etc., may be used. The mixture of components are added in any order that provides for the requisite binding. Incubations are performed at any suitable temperature typically between 4° C. and 40° C. Incubation periods are selected for optimum activity, but may also be optimized to facilitate rapid high-throughput screening. Typically between 0.1 and 1 hours will be sufficient.

Screening of Candidate Agents in an Animal Model

Agents having a desired activity as determined in the assays described above can be further screened for their ability to affect *Staphylococcus* virulence factor production, and to affect *Staphylococcus* infection, in a non-human animal model. The animal model selected will vary with a number of factors including, but not limited to, the particular pathogenic strain of Staphylococcus against which candidate agents are to be screened, the ultimate host for which the candidate agents are to serve as therapeutics, etc. Animals suitable for use in screening assays include any animal susceptible to infection by the selected *Staphylococcus* species. For example, where the *Staphylococcus* species is *S. aureus* or *S. epidermidis*, the animal model can be a rodent model, preferably a rat or a mouse model.

In general, the candidate agent is administered to a non-human animal susceptible to *Staphylococcus* infection, where the animal has been infected with *Staphylococcus* or receives an infectious dose of *Staphylococcus* in conjunction with the candidate agent. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired effect is to be achieved), topically, orally, or by any other desirable means. Normally, this screen will involve a number of animals receiving varying amounts and concentrations of the candidate agent (from no agent to an amount of agent that approaches an upper limit of the amount that can be delivered successfully to the animal), and may include delivery of the agent in different formulations. The agents can be administered singly or can be combined in combinations of two or more, especially where administration of a combination of agents may result in a synergistic effect. The agent can be used to coat a device that will then be implanted into the animal.

The effect of agent administration upon (the animal model can be monitored by any suitable method, such as assessing the number and size of *Staphylococcus*-associated lesions, microbiological evidence of infection, overall health, etc. Where the candidate agent affects *Staphylococcus* infection in a desirable manner (e.g., by reducing infectious load, facilitating lesion regression, etc.), the candidate agent is identified as an agent suitable for use in treatment of *Staphylococcus* infection.

Treating Bacterial Infection

The invention provides a method for preventing or treating a human or an animal susceptible to infection by certain bacterial infections (e.g., *S. aureus* in humans) by administering an agent that inhibits RAP or TRAP activity in facilitating virulence factor production, e.g., by inhibition RAP-mediated activation of RNAIII and subsequent virulence factor production.

The compounds having the desired pharmacological activity may be administered in a physiologically acceptable carrier to a host for treatment or prevention of pathogenic *Staphylococcus* infection. The therapeutic agents may be administered in a variety of ways, orally, topically, parenterally, e.g., subcutaneously, intraperitoneally, intravascularly, intrapulmonary (inhalation), etc. Depending upon the manner of introduction, the compounds may be formulated in a variety of ways. The concentration of therapeutically active compound in the formulation may vary from about 0.1-100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

In one embodiment, the host is treated by administration of RIP or with a RAP or TRAP inhibitor, such as an anti-RAP antibody, or both. In one embodiment the RAP inhibitor is co-administered with other RAP or TRAP inhibitors and/or co-administered with other inhibitors of Staphylococcal virulence, e.g., co-administered with RIP and/or with conventional antibiotics. In another embodiment a RAP or TRAP inhibitor, RIP, and a RAP or TRAP inhibitor (e.g., an anti-RAP or TRAP antibody) are administered. Such combination therapies (e.g., administration of multiple RAP inhibitory agents; administration of RAP and RIP; and/or administration of RAP or TRAP inhibitor, RIP, and/or TRAP or RAP inhibitor) may involve co-administration or sequential administration of the active components. The dosage regimen may be adjusted to provide the optimum therapeutic response. For example, several divided doses may be administered daily or the dose may be proportionally reduced as indicated by the therapeutic situation. The active compounds may be administered in any convenient manner, such as by oral, intravenous, intramuscular, subcutaneous, buccal, transdermal, or inhalation routes.

Formulations composed of RIP, RAP inhibitor, TRAP inhibitor, or a combination thereof, are administered at a therapeutically effective dosage, e.g., a dosage sufficient to improve the chance of successful prevention or treatment of infection. Administration of such a formulation can be via any of the accepted modes of administration for agents that serve similar utilities, preferably by systemic administration. Administration can include above combinations with other inhibitors, for example conventional antibiotics.

Human dosage levels for treating infections are known and generally include a daily dose from about 0.1 to 500.0 mg/kg of body weight per day, preferably about 6.0 to 200.0 mg/kg, and most preferably about 12.0 to 100.0 mg/kg. Generally, it is sought to obtain a serum concentration of such a formulation approximating or greater than circulating levels needed to reduce eliminate any infection in less than 10 days. For administration to a 70 kg person, the dosage range would be about 50 mg to 3.5 g per day, preferably about 100 mg to 2 g per day, and most preferably about 200 mg to I g per day. The amount of formulation administered will, of course, be dependent on the subject and the severity of the affliction, the manner and schedule of administration and the judgment of the prescribing physician.

In employing formulation for treatment of infections, any pharmaceutically acceptable mode of administration can be used. The formulations can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. The formulations can also be administered in sustained or controlled release dosage forms (e.g., employing a slow release bioerodable delivery system), including depot injections, osmotic pumps, pills, transdermal and transcutaneous (including electrotransport) patches, and the like, for prolonged administration of a predetermined rate, preferably in unit dosage forms suitable for single administration of precise dosages or, as discussed below, the coating of a device that is to be inserted into a body.

The compositions will typically include a conventional pharmaceutical carrier or excipient and a formulation of the invention. In addition, these compositions may include other active agents, carriers, adjuvants, etc. Generally, depending on the intended mode of administration, the pharmaceutically acceptable composition will contain about 0.1% to 90%, preferably about 0.5% to 50%, by weight of active compound, the remainder being suitable pharmaceutical excipients, carriers, etc. Actual methods of preparing such dosage forms are known, or will be apparent, to those skilled in this art. For example, see *Remington's Pharmaceutical Sciences*, Mack Publishing Company, Easton, Pa., $15^{th}$ Edition, 1975.

Parenteral administration is generally characterized by injection, either subcutaneously, intradermally, intramuscularly, or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of active ingredient contained in such parenteral compositions is highly dependent on the specific nature thereof, as well as the needs of the subject. However, percentages of active ingredient of 0.01% to 10% in solution are employable, and will be higher if the composition is a solid which will be subsequently diluted to the above percentages. Preferably, the composition will comprise 0.2-2% of the active ingredient in solution.

A more recently devised approach for parenteral administration employs the implantation of a slow-release or sustained-release system, such that a constant level of dosage is maintained. Various matrices (e.g., polymers, hydrophilic gels, and the like) for controlling the sustained release, and for progressively diminishing the rate of release of active agents are known in the art. See U.S. Pat. No. 3,845,770 (describing elementary osmotic pumps); U.S. Pat. Nos. 3,995,651, 4,034,756 and 4,111,202 (describing miniature osmotic pumps); U.S. Pat. Nos. 4,320,759 and 4,449,983 (describing multichamber osmotic systems referred to as push-pull and push-melt osmotic pumps); and U.S. Pat. No. 5,023,088 (describing osmotic pumps patterned for the sequentially timed dispensing of various dosage units).

Fornnulations of active components may also be administered to the respiratory tract as a nasal or pulmonary inhalation aerosol or solution for a nebulizer, or as a micro fine powder for inhalation, alone or in combination with an inert carrier such as lactose, or with other pharmaceutically acceptable excipients. In such a case, the particles of the formulation may advantageously have diameters of less than 50 microns, preferably less than 10 microns. See e.g., U.S. Pat. No. 5,364,838, which discloses a method of administration for insulin that can be adapted for the administration of formulations of the present invention.

Vaccination

The invention provides a vaccine for inoculating a human or an animal susceptible to infection by certain bacterial infections (e.g., *S. aureus* and *S. epidermidis*) by administering RAP, TRAP, or an antigenically effective portion of RAP or TRAP, in a pharmaceutically acceptable carrier, which may optionally comprise an adjuvant. Formulations appropriate for elicitation of the immune response are well known in the art. In general, the host is exposed to the antigen, such as RAP or TRAP, which perturbs the host's immune system and results in an immune response towards the antigen. An adjuvant can be added with the antigen to increase the immune response to the antigen. The amount of polypeptide administered is an amount sufficient to elicit a protective immune response in the host. Methods for determining such appropriate amounts are routine and well known in the art. For example, RAP, TRAP and/or antigenically effective portion(s) thereof can be used to vaccinate an animal model of *Staphylococcus* infection. The amounts effective in such animal models can be extrapolated to other hosts (e.g., livestock, humans, etc.) in order to provide for an amount effective for vaccination.

Vaccination of Animals with Recombinant RAP (rL2)

4 week old female Balb/C mice (ten mice/group) were injected subcutaneously on days 0, 7, 21 with 50 μg rL2 (50 μg/50 μl PBS) together with 50 μl complete Freund's adjuvant on first injection and incomplete Freund's adjuvant on second and third injections. Control animals were injected with adjuvant/PBS only. Animals were challenged on day 35 with $2\times10^9$ Smith Diffuse *S. aureus* (SD) prepared as described below. Animals were observed daily for mortality, overall health and development of lesion. The size of the lesion was measured as (area=0.5 n (length)(width)).

Preparation of bacteria for challenge: Smith Diffuse *S. aureus* was grown overnight at 37° C. on blood agar plates. Bacteria were suspended in PBS at $2\times10^{10}$ cells/ml. $2\times10^9$ (100 μl) cells were injected to vaccinated and control animals subcutaneously, together with 1 mg cytodex beads, to induce a local infection.

Antibody level as determined by ELISA: A drop of blood was collected from the tip of the tail before the first vaccination and 10 days after the third vaccination. ELISA plates were coated overnight with 50 μl of 25 μg/ml antigen or with 3% BSA as a control. Wells were then blocked with 3% BSA for 3 hrs at room temperature, and 50 μl sera (diluted 1:1000 in PBS) was applied for 2.5 hrs at room temperature. Unbound antibody was removed and wells were washed 5×2 min with PBS with 0.05% TWEEN 20. 50 μl peroxidase-conjugated anti-mouse antibody (Sigma) diluted 1:2000 with PBS/TWEEN was applied for 1 hr at 37° C. Unbound antibody was removed, and wells were washed as above, and bound antibody was detected by ABTS (Sigma) according to the manufacturer's instructions.

Results of Vaccination Experiments

Development of antibody to the antigen: All vaccinated animals developed an antibody titer (>1000) to the injected antigen. None of the control animals had a detectable antibody level to the injected antigen.

Mortality post challenge: As shown in FIG. 4, of 10 control animals vaccinated with adjuvant only 3 animals died within the first day post challenge, and another mouse died on the second day. Of 10 animals vaccinated with rL2, none died within the first day, one died on the second day and another died on the third day.

Lesion: All surviving animals developed a lesion and its size was determined on the fifth day post challenge. As shown in FIG. 5, the average lesion size of control animals was 7 $cm^2$, while the average lesion size of animals vaccinated with rL2 was only 2.5 $cm^2$.

Conclusions: Animals vaccinated with rL2 had delayed mortality and a 50% reduction in mortality rate, and a 65% reduction in lesion size. These results suggest that rL2 can confer protection to a S. aureus infection. Of note is the fact that the number of bacteria used for challenge was exceptionally high and it is expected that if a lower number of bacteria were present, protection level from infection could be higher.

CONCLUSION

RAP (native or recombinant) inhibits RNAIII synthesis in vitro and protects animals from *S. aureus* infection in vivo. Because RAP is a homolog of L2, which is found in all bacteria, RAP can serve as a target site for therapy to various bacterial infections in addition to *S. aureus*.

Coated Devices

The invention provides for a device, the surface of which is coated with a composition having an amount of a RAP inhibitory agent (e.g., an anti-RAP or anti-TRAP antibody, inhibitory peptides, RIP peptide or RIP derivative peptides) effective to inhibit biofilm formation by *Staphylococci* or by other bacterial expression RAP, TRAP or RAP-like or TRAP-like molecules. The coated device may be any device which may be associated with a risk of *Staphylococcus* or other bacterial infection or exposure of a host (e.g., surgery patient, menstruating female, etc.), to *Staphylococcus* virulence factors.

Coated devices encompassed by the present invention include, but are not limited to, catheters, needles, surgical instruments (e.g., scalpels, sponges, retractors, etc.), bandages and bandage materials (e.g., gauze dressings, etc.), artificial joints, heart valves, and tampons, or any other medical device. Such devices have a tendency to bring *Staphylococci* or other bacteria into contact with the host, or to attract colonizations by staph bacteria (e.g., tampons), in such situations, the coated devices may prevent or reduce *Staphylococcus* or other bacterial infection, or prevent or reduce the development of serious symptoms associated, e.g., with exposure to *Staphylococcus* virulence factors.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

I claim:

1. A method of treating or reducing the risk of *Staphylococcus aureus* bacterial infection in a mammal, said risk presented by the insertion of a medical device in the mammal comprising providing said medical device with a coating that comprises an RNAIII inhibiting peptide (RIP) and inserting the device into the mammal, where the coating reduces the risk of *S. aureus* infection presented by said insertion of the medical device.

2. The method of claim 1, wherein said medical device is a suture, arteriovenous shunt, schleral buckle, endotracheal tube, vascular graft, orthopedic device, prosthesis, bandage, bandage material, catheter, needle, surgical instrument, artificial joint, heart valve, or tampon.

3. The method of claim 1, wherein said medical device is soaked in a solution comprising an effective amount of RIP prior to insertion of said device in said mammal.

* * * * *